United States Patent
Vogt et al.

(10) Patent No.: US 7,074,386 B2
(45) Date of Patent: Jul. 11, 2006

(54) PRESSURE INDUCED SWELLING IN MICROPOROUS MATERIALS

(75) Inventors: Thomas Vogt, Wading River, NY (US); Joseph A. Hriljac, Birmingham (GB); Yongjae Lee, Yaphank, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 69 days.

(21) Appl. No.: 10/303,169

(22) Filed: Nov. 25, 2002

(65) Prior Publication Data

US 2004/0115269 A1 Jun. 17, 2004

(51) Int. Cl.
*A61K 51/00* (2006.01)
*A61M 36/14* (2006.01)

(52) U.S. Cl. .................... 424/1.29; 424/1.11; 424/450; 424/489

(58) Field of Classification Search ............... 424/1.11, 424/1.65, 489, 450, 9.1, 9.3, 1.29, 1.37; 128/653.2
See application file for complete search history.

(56) References Cited

U.S. PATENT DOCUMENTS 5,122,363 A    6/1992  Balkus, Jr. et al.
2004/0115269 A1 * 6/2004 Vogt et al. ................. 424/484

OTHER PUBLICATIONS

Lee et al, "First Structural Investigation of a Super-Hydrated Zeolite", J. Am. Chem. Soc., 2001, 123, pp. 12732-12733.*
Lee et al., "Non-Framework Cation Migration and Irreversible Pressure-Induced Hydration in a Zeolite," *Nature*, vol. 420, pp. 485-489, (Published on Web Dec. 5, 2002).
Lee et al., "Phase Transition of Zeolite RHO at High-Pressure," *J. Am. Chem. Soc.*, vol. 123, pp. 8418-8419, (Published on Web Aug. 3, 2001).
Lee et al., "First Structural Investigation of a Super-Hydrated Zeolite," *J. Am. Chem. Soc.*, vol. 123, pp. 12732-12733, (Published on Web Nov. 22, 2001).
Lee et al., "Pressure-Induced Volume Expansion of Zeolites in the Natrolite Family," *J. Am. Chem. Soc.*, vol. 124, pp. 5466-5475, (Published on Web Apr. 18, 2002).
Moroz et al., "Pressure-Enhanced Molecular Self-Diffusion in Microporous Solids," *Microporous and Mesoporous Materials*, vol. 42, pp. 113-119 (2001).
Frillette et al., "Catalysis by Crystalline Aluminosilicates: Characterization of Intermediate Pore-Size Zeolites by the 'Constraint Index,'" *Journal of Catalysis*, vol. 67, pp. 218-222 (1981).

* cited by examiner

*Primary Examiner*—Dameron L. Jones
(74) *Attorney, Agent, or Firm*—Margaret C. Bogosian

(57) ABSTRACT

A method for capturing specified materials which includes contacting a microporous material with a hydrostatic fluid having at least one specified material carried therein, under pressure which structurally distorts the lattice sufficiently to permit entry of the at least one specified material. The microporous material is capable of undergoing a temporary structural distortion which alters resting lattice dimensions under increased ambient pressure and at least partially returning to rest lattice dimensions when returned to ambient pressure. The pressure of the fluid is then reduced to permit return to at least partial resting lattice dimension while the at least one specified material is therein. By this method, at least one specified material is captured in the microporous material to form a modified microporous material.

20 Claims, 13 Drawing Sheets

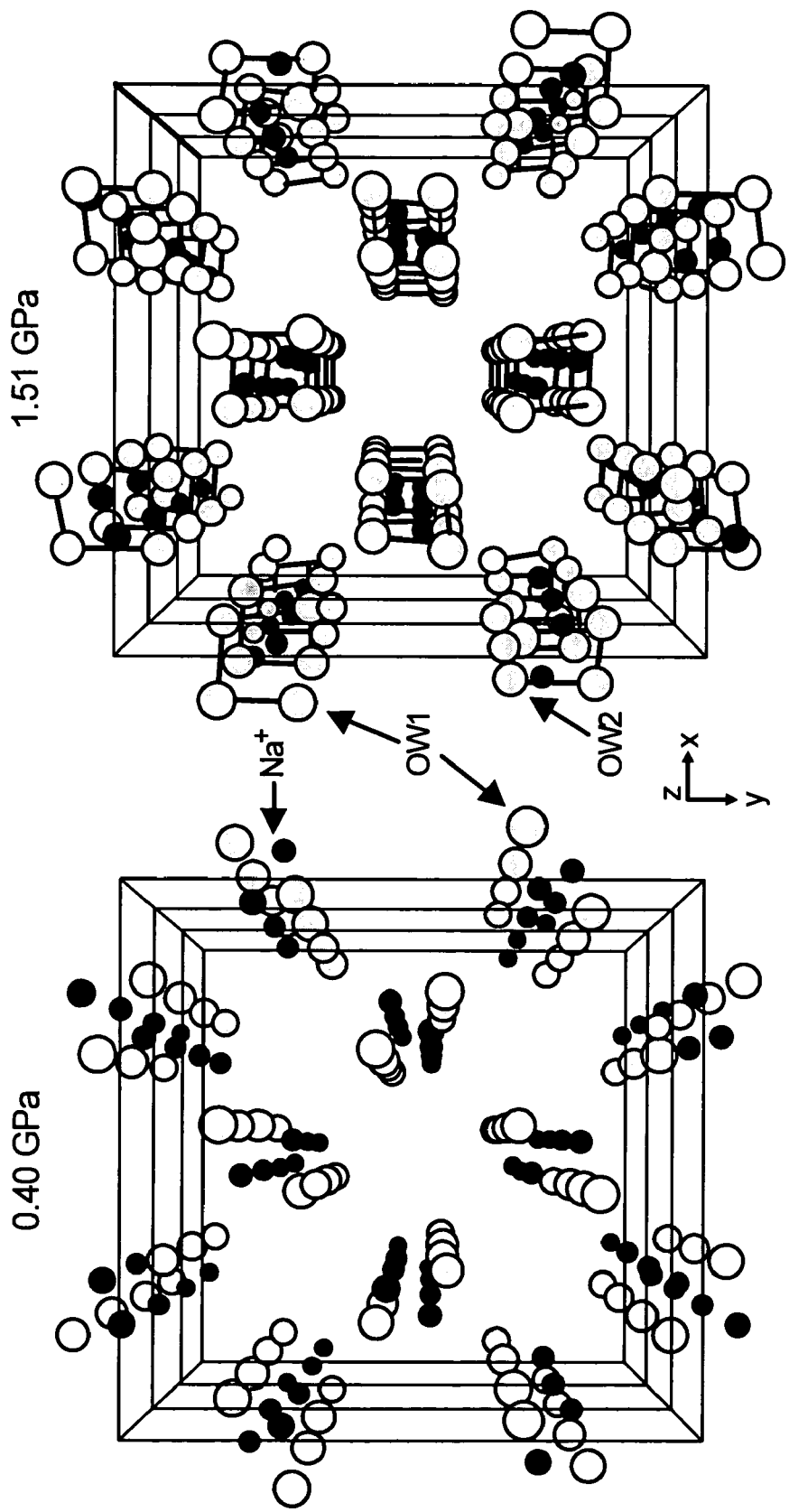

PRESSURE INDUCED SWELLING IN MICROPOROUS MATERIALS

This invention was made with Government support under contract number DE-AC02-98CH10886, awarded by the U.S. Department of Energy. The Government has certain rights in the invention.

BACKGROUND OF THE INVENTION

The present invention relates to the art of microporous materials, especially zeolites, and, in particular, to new methods of treating such materials, and to the products resulting from such treatment.

Certain microporous materials, especially zeolites, are unique minerals which were formed millions of years ago as a result of volcanic activity beneath ancient desert lakebeds. The awesome forces of nature combined to form this remarkable family of minerals which absorb and release water vapor and absorb specific gas molecules. The physical structures of zeolites and similar microporous materials are arranged in an interconnecting framework structure. This structure is arranged to form a honeycomb framework of interconnecting channels that are consistent in diameter. The diameter of these open channels is what differentiates each type of microporous material, such as the zeolite family, and is what gives rise to their unique properties. Within these channels are positively charged ions (cations) attached and held by the framework's negative charge.

Microporous materials, especially zeolites, can be used to perform a variety of functions. They can be used for water absorption/desorption and have the ability to absorb/desorb water vapor without toplogical change in the interconnecting framework structure. Some microporous materials, such as zeolites, also have the ability to selectively absorb specific gas molecules without any effect. In addition, microporous materials, most notably zeolites, are some of the most efficient ion exchangers known. They have the ability to exchange one cation for another determined by ion size and channel diameter.

Zeolites are naturally occurring aluminosilicate materials crystallizing in a variety of low-density framework structures constructed from corner-connected (Al,SiO$_4$)-tetrahedra. These units define windows with a narrow size-distribution of pores and channels of molecular dimensions. It is the restricted access to the interior that provides the reactant-, transition state and product-selectivity. This selectivity makes these "nanoreactors" valuable selective heterogeneous catalysts and ion exchangers in a number of industrial and environmental applications. The built-in flexibility of the T-O-T angle connector between tetrahedral units allows these structures to contract and expand in response to thermodynamic variables such as temperature and pressure. Other microporous materials have structures similar to zeolites and share many of the same properties of zeolites. These microporous materials are often referred to as zeolite-like materials.

While an ever-expanding variety of microporous materials with a wide range of pore sizes is available, it is desirable to have a way to vary the chemistry of the nanopores for a given framework topology and provide selective access to the interior for ion exchange and sorption. Temperature has been used almost exclusively to control the degree of hydration and hydroxylation, remove templating molecules after synthesis, facilitate ion exchange or gas separation processes or to control the cation distributions within the pores. However, modifications of the nanopores using temperature may compromise the mechanical integrity of the whole atomic scaffolding, and indeed, in many cases the metastable frameworks collapse to dense structures below the corresponding glass transition temperatures, the upper limit for the temperature-driven applications. For those classes of microporous materials with relatively dense framework structures, such as natrolite and related analogues, the limited access to the internal pores makes facile and reversible tuning of the nanopore chemistry, using temperature alone, difficult.

Accordingly, there is a need for a way to vary the chemistry of the nanopores for a given framework topology without damaging or destroying the interconnecting framework structure.

SUMMARY OF THE INVENTION

In accordance with the present invention, a method for capturing specified materials and the microporous material formed thereby are provided. For the purposes of the present invention, the term specified material and microscopic agent are used interchangeably and refer to the material captured in the microporous materials. The specified materials can be atoms, molecules, ions or a combination thereof. The method includes contacting a microporous material with a hydrostatic fluid having at least one specified material carried therein, under pressure which structurally distorts the lattice sufficiently to permit entry of the at least one specified material. The microporous material is capable of undergoing a temporary structural distortion which alters resting lattice dimensions under increased pressure at ambient temperature and at least partially returning to rest lattice dimensions when returned to ambient pressure. The pressure of the fluid is then reduced to permit return to at least partial resting lattice dimension while the at least one specified material is therein. By this method, at least one specified material is captured in the microporous material to form a modified microporous material. In a preferred embodiment, the modified microporous material has an increased number of water molecules. The microporous material is preferably a zeolite or a potassium gallosilicate, which begin to swell instantaneously with increased pressure at ambient temperature. Preferably, the swelling of the microporous materials is substantially completed within less than five (5) minutes at the increased pressure.

The hydrostatic fluid can be water. More preferably the hydrostatic fluid includes water and methanol, water and ethanol or a combination of water, methanol and ethanol. In preferred embodiments, the hydrostatic fluid comprises from about 50 to about 95 weight percent methanol, from about 5 to about 40 weight percent ethanol and from about 1 to about 25 weight percent water and most preferably from about 75 to about 85 weight percent methanol, from about 10 to about 25 weight percent ethanol and from about 2 to about 8 weight percent water.

The preferred microporous materials for the present invention are a Zn-containing form of Linde A zeolite having the molecular structure $Zn_6[Al_{12}Si_{12}O_{48}]$ 29H$_2$O, a lithium exchanged Linde A zeolite, having the molecular structure $Li_{12}[Al_{12}Si_{12}O_{48}]$ 29H$_2$O, potassium gallosilicate ($K_{16}Ga_{16}Si_{24}O_{80}$·12H$_2$O), natrolite ($Na_{16}Al_{16}Si_{24}O_{80}$·16H$_2$O), a gallosilicate analogue of natrolite ($Na_{16}Al_{16}Si_{24}O_{80}$·16H$_2$O), scolecite ($Ca_8Al_{16}Si_{24}O_{80}$·24H$_2$O) and mesolite ($Ca_8Al_{16}Si_{24}O_{80}$·24H$_2$O). The Zn-containing form of Linde A zeolite captures specified materials when the pressure is increased and the structure continues to swell up to about 0.6 gigapascals (GPa). Above 0.6 GPa, the Zn-containing form of Linde A zeolite structure contracts and the specified materials are "pressed out." The lithium exchanged Linde A zeolite captures specified materials when the pressure is increased up to between about 1.5 to about 2.0 GPa. Potassium gallosilicate captures specified materials when the pressure is increased up to between about 1 to about 2 GPa; natrolite captures specified materials when the pressure is increased up to between about 0.8 to about 1.5 GPa; scolecite captures specified materials when the pressure is increased up to between about 2 to about 3 GPa; and mesolite captures specified materials when the pressure is increased up to between about 1.2 and 1.7 GPa. An especially preferred gallosilicate analogue of natrolite ($Na_{16}Ga_{16}Si_{24}O_{80} \cdot 16H_2O$) captures specified materials when the pressure is increased up to between about 0.35 and 0.6 GPa.

The specified materials that are captured by the method of the present invention can be large cations, preferably $Pb^{2+}$, $Gd^{3+}$, $Hg^{2+}$, $Cd^{2+}$, $Sr^{2+}$, $Cs^+$, $Ag^+$, $Ba^{2+}$, $Er^{3+}$, $Eu^{3+}$, $K^+$, $Er^{3+}$, $Eu^{3+}$, $K^+$, $La^{3+}$, $NH_4^+$, $Na^+$, $Pd^{2+}$, $Rb^{2+}$, $Sn^{2+}$, $Te^{4+}$, $Tl^+$, $Tm^{3+}$, $Y^{3+}$, $Yb^{3+}$ or $Zn^{2+}$. After the specified materials are captured in the microporous materials according to the present invention, the modified microporous material which is formed has a unit cell volume greater than the unit cell volume of the microporous material. The specified cations remain incorporated in the modified microporous material at pressures after the ambient pressure is decreased to below about 0.1 GPa.

In one embodiment, the present invention relates to a microporous material product that includes a microporous material capable of undergoing temporary lattice-enlarging structural distortion which alters resting lattice dimensions under increased pressure at ambient temperature, and at least partially returning to rest-lattice dimensions when returned to standard temperatures and pressure (STP) conditions; and a microscopic agent captured in the pores of the microporous material, the agent unable to enter into the lattice of the microporous material at STP, whereby the product is provided. The preferred microporous materials are listed above. In a particularly preferred embodiment, the microscopic agent captured in the pores include large cations, most preferably $Pb^{2+}$, $Gd^{3+}$, $Hg^{2+}$, $Cd^{2+}$, $Sr^{2+}$, $Cs^+$, $Ag^+$, $Ba^{2+}$, $Er^{3+}$, $Eu^{3+}$, $K^+$, $La^{3+}$, $NH_4^+$, $Na^+$, $Pd^{2+}$, $Rb^{2+}$, $Sn^{2+}$, $Te^{4+}$, $Tl^+$, $Tm^{3+}$, $Y^{3+}$, $Yb^{3+}$, or $Zn^{2+}$. The microporous material product has a unit cell volume greater than the unit cell volume of the microporous material.

In another embodiment, the present invention relates to a system for capturing a microscopic agent in a microporous material. The system includes a chamber arranged to permit controlledly increasing and decreasing pressure in the chamber; a liquid system comprising a liquid capable of transmitting changes in pressure and a microscopic agent, wherein the liquid system is contained in the chamber; a microporous material having pores comprising a three-dimensional lattice structure, the pores having resting lattice dimensions and capable of lattice distortions under increased ambient pressure; and an applied pressure, preferably up to about 5 GPa, on the liquid sufficient to distort the lattice, wherein the distortions are sufficient to admit the agent into the pores of the microporous material; wherein the microscopic agent is captured in the pores when the chamber is returned to standard temperature and pressure conditions. The preferred microporous material and microscopic agent are described above. The preferred liquid is an aqueous liquid. The lattice distortions occur along either two or three axes of the lattice.

The present invention also relates to a contrast or image-brightening agent and an imaging method using the agent. The contrast or image-brightening agent includes a microporous material, capable of undergoing a temporary structural distortion which alters resting lattice dimensions under increased ambient pressure and at least partially returning to rest lattice dimensions when returned to ambient pressure and a paramagnetic ion captured in the microporous material. The paramagnetic ion can include a rare earth element or a transition metal ion. Preferred paramagnetic ions are $V^{4+}$, $Cu^{2+}$, $V^{3+}$, $Ni^{2+}$, $Cr^{3+}$, $Co^{2+}$, $Fe^{2+}$, $Co^{3+}$, $Mn^{2+}$ and $Fe^{3+}$ and $Gd^{3+}$.

The imaging method includes administering to an animal, preferably a human, an amount of a paramagnetic ion captured in a microporous material that is effective as a contrast or image-brightening agent. The microporous material and paramagnetic ion included in the contrast or image-brightening agent are described above.

The modified microporous structures of the present invention possess unique properties which allow them to be used in a variety of applications. Some of the advantages of the microporous structures of the present invention are:

Immobilization of radioactive and/or toxic ions under pressure, such as $Pb^{2+}$, $Hg^{2+}$ and $Cd^{2+}$. Under ambient conditions, up to about 11% Cd can be incorporated in natrolite but under the high pressure conditions of the present invention, up to about 50% Cd can be incorporated.

Medical magnetic resonance imaging (MRI) relies on having the patients swallow imaging contrast agents. These contrast agents contain high-spin metals that bind the water and thereby lead to proton spin relaxation times which are orders of magnitude faster than those obtained with "free" water. Gadolinium ions ($Gd^{3+}$) work very well as contrast agents, but cannot be administered directly due to their toxicity. However, $Gd^{3+}$ contained in nanopores of zeolites and clays work very well. See, U.S. Pat. No. 5,122,363 by Balkus et al., which is incorporated herein in its entirety. Zeolites are not toxic when introduced into the gastrointestinal tract and, when used in medical applications, mitigate the toxicity of metals such as $Gd^{3+}$. The modified microporous structures of the present invention provide the advantage of increased security with respect to metal ions exchanging while in the human body. The "trap-door-mechanism" reduces this possibility significantly due to the pores and windows being too small at ambient pressure to permit passage out of the structures and into the body.

"High pressure drying", i.e. separation of minute amounts of water from organic chemicals which would degrade if the water was removed by distillation or conventional drying methods.

Water transport to and from high pressure regions in soil or granular matter.

Li-A coatings on glass or silicon substrates show no compressibility up to 15 kbar when used as a membrane in the presence of water. This mechanical stability under pressure could be desirable in submarine applications. There are more and more uses of zeolites as membranes in thin film form. Mechanical stability is crucial. If not, film peels off after numerous pressure cycles.

BRIEF DESCRIPTION OF THE FIGURES

Other objects and many attendant features of this invention will be readily appreciated as the invention becomes better understood by reference to the following detailed description when considered in connection with the accompanying drawings wherein:

FIG. 8 is a structure of the non-framework species found in natrolite at 0.40 GPa viewed perspective along the c-axis.

FIG. 9 is a structure of the non-framework species found in natrolite at 1.51 GPa viewed perspective along the c-axis.

DETAILED DESCRIPTION OF THE INVENTION

Figure 1:
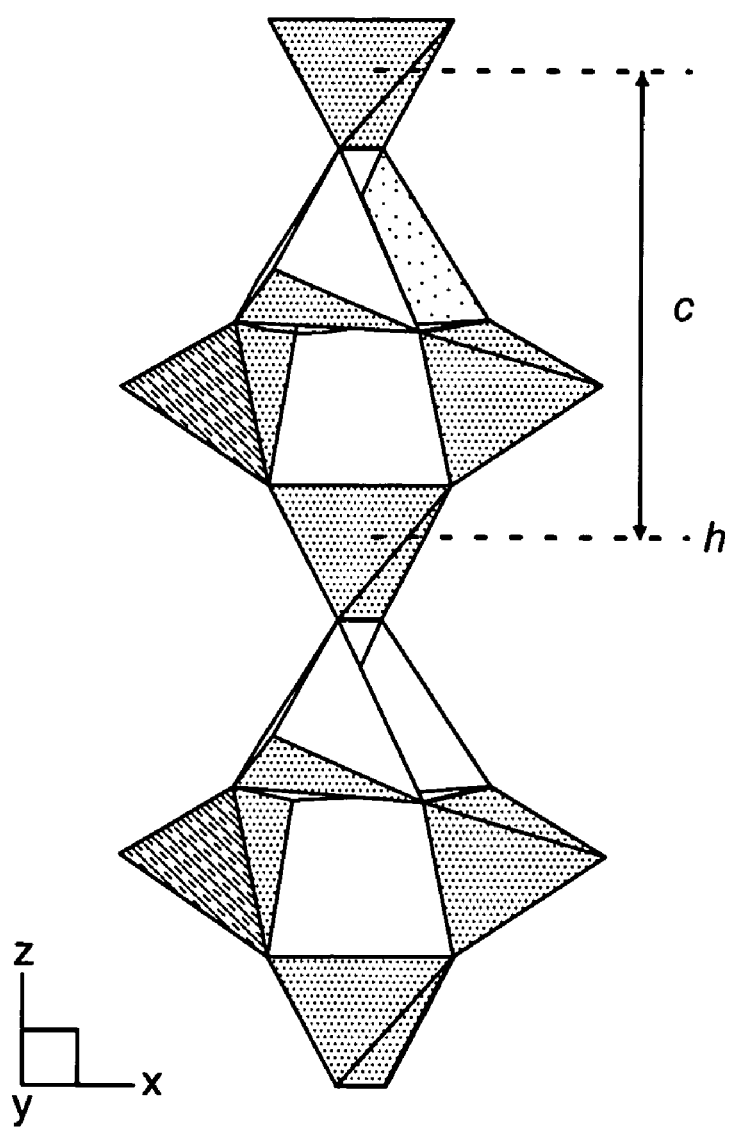
FIG. 1 shows a polyhedral representation of the chain found in the natrolite framework with the repeat distance of the $T_5O_{10}$ building unit of the Si- (shaded) and Al- (unshaded) tetrahedra constituting the c-axis length (c).

The present invention relates to microporous materials, especially zeolitic systems, which can take up water under pressure and increase their volumes while maintaining their symmetry.

Most materials are compacted or fall apart under pressure. However, the microporous materials of the present invention have been found to expand under pressure when in contact with a fluid. Because of this characteristic, these unusual materials can function as "molecular sponges" for soaking up chemical pollutants or even radioactive waste.

The superhydrated microporous systems formed by the pressure-induced expansion of microporous materials can be used to set up a "trap door" mechanism for locking up chemical or radioactive pollutants. When the pressure is increased, the material, as well as the pores of the material, get bigger. This allows larger ions or molecules, such as hydrocarbons, mercury, lead, or even radioactive atoms, such as strontium, to enter the pores of the material. These larger ions or molecules are referred to as "guest materials" or "guests." Then, when the pressure is released, the size of the pores decreases and the guest materials are trapped or "captured" inside the interconnecting framework structure.

In one embodiment of the present invention, the guest materials are pollutants that need to be removed from a "host material." For example, the pollutants may be hydrocarbons that are contaminating groundwater or radionuclides in the cooling water of a nuclear power plant.

In general, the microporous materials are capable of capturing specified (or "guest") materials which are too large to enter into the pores of the microporous materials at standard temperature and pressure conditions, but which are small enough to enter into the pores of the microporous materials when the lattices of the microporous materials have been sufficiently distorted by increasing the pressure.

When solids are pressurized in a hydrostatic medium, the unit-cell volume will normally decrease. A few select materials remain crystalline but the volumes increase with applied pressure, presumably due to the uptake of molecules into the solid from the pressure-transmitting medium. The members of the small-pore natrolite (NAT) family are the only zeolite systems that are known to display pressure-induced expansion (PIE), and for the parent natrolite it has been shown that water uptake into discrete crystallographic sites to form a superhydrated material is the underlying mechanism for expansion. It has now been found that PIE occurs in a zeolite that is not in the NAT family, specifically the Zn-exchanged form of zeolite A (LTA). Unlike the NAT materials, the LTA structure displays cation-dependent behavior as the Na and Ca forms undergo normal contraction. Since all three materials have the same framework topology and essentially identical water contents, it is believed that a complex mechanism involving more than simple water insertion must occur.

Zeolite A has been widely used in scientific studies of framework solids as it has a 1:1 Si/Al ratio, cubic symmetry and a uniform three-dimensional pore system. The chemical composition of the as-synthesized sodium form (Na-A) is $Na_{12}[Al_{12}Si_{12}O_{48}]\cdot27H_2O$, and the sodium cations may be readily exchanged to produce systems such as Zn-A, $Zn_6[Al_{12}Si_{12}O_{48})\cdot29H_2O$, or Ca-A, $Ca_6[Al_{12}Si_{12}O_{48}]\cdot28H_2O$. The charge-balancing cations sit in well-defined locations within the pores, and typically interact with both framework and water oxygen atoms. The exact locations and cation-oxygen interactions vary with the type of cation, and these also lead to changes in the size of the cubic unit cell.

The pressure-induced expansion of microporous materials varies for different materials since interconnecting framework structures respond differently to an increase in pressure. For example, it has been found that in a Zn-containing form of Linde A, $Zn_6[Al_{12}Si_{12}O_{48}]$ $29H_2O$, the volume of the unit cell increases with applied hydrostatic pressures up to about 0.6 GPa. After further pressure increase, the PIE (also referred to as pressure induced swelling (PIS)) gives way to a decrease of cell volume. In contrast, in lithium exchanged Linde A, $Li_{12}[Al_{12}Si_{12}O_{48}]$ $29H_2O$, there is no increase of the unit cell and, therefore, no compressibility up to about 1.5 GPa. Thereafter, up to about 2 GPa a small increase is observed, followed by the decreased unit cell volume as the hydrostatic pressure continues to increase.

The crystal chemistry of microporous materials, especially zeolites, under moderately high-pressures (defined herein as below 5 GPa) is not similar to that observed in temperature-dependent studies. The present invention relates to the change in the structures of microporous materials, such as zeolites, at increased hydrostatic pressures. For example, inverse-pressure effects such as anomalous volume expansion and an increase in water diffusivity have been found in natrolite and its analogues, the mechanism of which was previously unknown.

The terms "hydrostatic fluid" and "hydrostatic pressure transmitting fluid" are used interchangeably herein and refer to the fluid which is used to transmit the pressure to the microporous materials. Although "hydrostatic fluids" are used herein to demonstrate the effect of increased pressure on the microporous materials of the present invention, the effect is not limited to hydrostatic fluids. The effect can also be achieved using non-hydrostatic fluids and non-hydrostatic conditions do not suppress the effect. In order to be useful in the present invention, the molecules of the fluid (whether a hydrostatic fluid or a non-hydrostatic fluid) must be smaller than the size of the pores of the microporous material being used at their maximum expansion. This permits the molecules of the fluid to enter the microporous structures.

Pressure conveyed through a hydrostatic pressure transmission fluid can be used to alter the crystal structures of microporous materials without leading to a collapse of the framework. In addition to altering the crystal structures, the increased pressure alters the nanopore chemistry of the microporous materials via interactions with the hydrostatic pressure transmission fluid. For example, it has been found that the compressibility and phase transition kinetics of zeolite rho are dependent upon the charge compensating cations and their distributions within the pores. In addition, it has been found that the volume expansion of natrolite at high-pressure (above 1.2 Gpa) occurs through selective sorption of water molecules from the hydrostatic pressure fluid, giving rise to a superhydrated phase with twice the water content. This anomalous volume expansion at high pressure is particularly intriguing since it results in the formation of a new water structure inside the walls of the nanochannels and is responsible for the increased water diffusion at high pressures. In addition, the expanded pore openings resulting from the channel swelling under pressure has been found to dramatically alter the ion exchange and other sorption properties of this small-pore zeolite.

For the purposes of the present invention, the term "microporous materials" is used to refer to zeolites and non-zeolite analogues. Pore sizes of 2 nm or below are micropores, those in the range of 2 to 50 nm are mesopores and those above 50 nm are macropores. The term "resting lattice dimensions" refers to the spatial configuration of the interconnecting framework structure of a microporous material under ambient pressure and temperature conditions.

Figure 2:
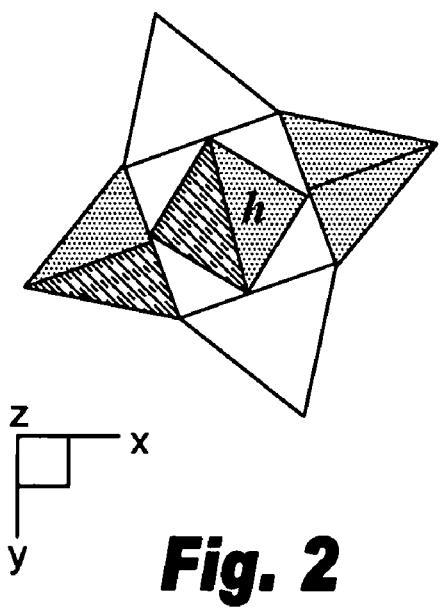
FIG. 2 shows a 4-connected tetrahedral node found in a natrolite framework that includes silicon and aluminum atoms.
Figure 3:
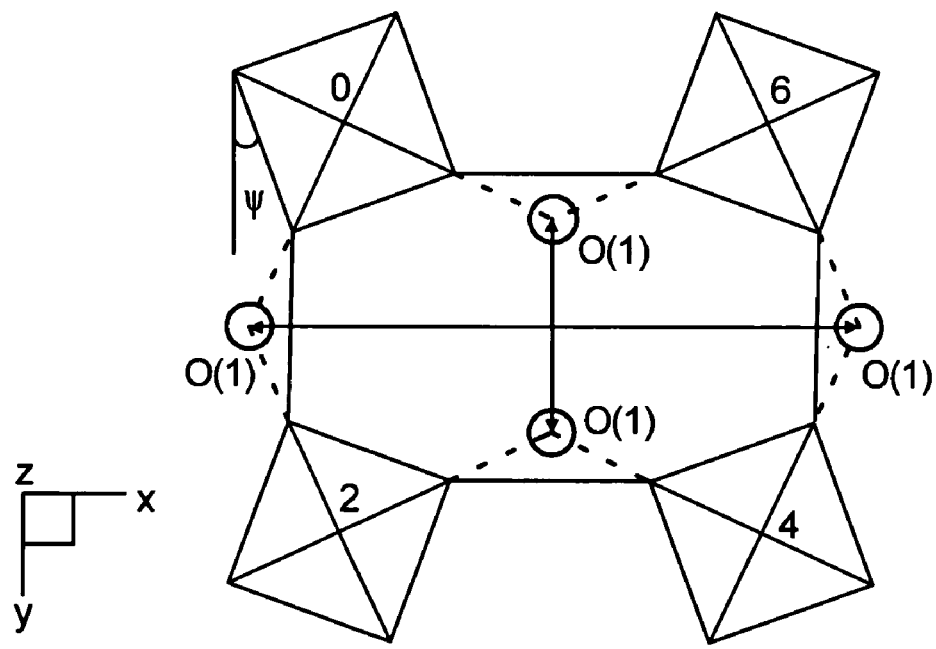
FIG. 3 is a skeletal representation showing the 2460-type connectivity of the neighboring chains of natrolite.

The microporous materials natrolite, mesolite and scolecite belong to the group of fibrous, small-pore zeolites with a natrolite topology. The framework is composed of $T_5O_{10}$ building units formed from linking five $TO_4$ tetrahedra (T=Al, Si, Ga . . . ). These units are then connected along the c-axis to form the so-called natrolite chains as shown in FIG. 1. The repeat distance of the $T_5O_{10}$ building unit of the Si- (shaded) and Al- (unshaded) tetrahedra constitutes the c-axis length (c). The mode of linkage of the chains to each other is conveniently described by the heights in eighths of a unit cell translation above the xy-plane of the central tetrahedral nodes of the $T_5O_{10}$ building units. In FIG. 2, the height of the central tetrahedral node is shown as h. Natrolite shows a 2460-type connectivity of the four neighboring chains (skeletal representation) as depicted in FIG. 3. As a result, helical 8-ring channels are formed along the c-axis with $T_{10}O_{20}$ windows intersecting perpendicular to these channels. The flexible linkages between and within the chains and their interactions with charge-balancing cations and water molecules give rise to various structural distortions depending on composition and temperature. A distortion parameter, $\psi$, which measures the average angle between the $T_5O_{10}$ building unit and the a- and b-unit-cell axes, can specify the degree of chain rotation. Under ambient conditions, the aluminosilicate natrolite (ideal chemical composition: $Na_{16}Al_{16}Si_{24}O_{80}.16H_2O$) has an ordered distribution of Al and Si over the T-sites in Fdd2 (orthorhombic) symmetry with sodium cations along the channels and water molecules close to the $T_{10}O_{20}$ windows.

Scolecite ($Ca_8Al_{16}Si_{24}O_{80}.24H_2O$) is a natural Ca-end-member of natrolite where the substitution of all Na cations by Ca and water causes a lowering of the unit cell symmetry from orthorhombic Fdd2 to pseudo-orthorhombic Fd (monoclinic). Mesolite ($Na_{5.33}$ $Ca_{5.33}Al_{16}Si_{24}O_{80}.21.33$ $H_2O$) is a natural analogue of natrolite where two-thirds of the Na cations in natrolite are replaced by Ca and $H_2O$. The structure of mesolite is composed of one natrolite-like and two scolecite-like layers alternating along the b-axis, resulting in a superlattice structure ($b_{mesolite}=3b_{natrolite}$) with Fdd2 symmetry and a tripling of the unit cell composition to $Na_{16}Ca_{16}Al_{48}Si_{72}O_{240}.64H_2O$. The potassium gallosilicate ($K_{16}Ga_{16}Si_{24}O_{80}.12H_2O$) is a synthetic natrolite where Na and Al are substituted by K and Ga, respectively. The resulting crystal structure differs from natrolite by a disordered distribution of Ga and Si over the framework tetrahedral sites to give rise to a $I\bar{4}$ 2d (tetragonal) symmetry and a unit cell composition of $K_8Ga_8Si_{12}O_{40}.6H_2O$. In contrast to the Na and $H_2O$ distribution in natrolite, potassium cations occupy the sites bound by the $T_{10}O_{20}$ windows close to the channel walls and water molecules are found along the channels.

Natrolite and the related analogues are examples of small-pore zeolites into which both cation and water access are hindered due to the small-pore size. Most of the studies on the cation exchange properties of these structures show that a very limited exchange occurs in aqueous solutions below 100° C. and that the highest exchange levels occurred in fused salt studies. Large radioisotopes such as $^{90}$Sr and $^{137}$Cs are simply too large to access the narrow pores of natrolite at ambient conditions. It is also well known that natrolite does not take up any significant amounts of smaller transition metal cations such as Co, Ni, Cd and Zn.

Although mesolite and scolecite are calcium-containing members of the natrolite group, substitution of sodium with calcium is not possible under normal ion exchange conditions. The reason is believed to be the unusual sevenfold coordination environment for calcium and other divalent cations in the natrolite framework as opposed to the preferred six-fold coordination of sodium, which makes the substitution of two sodium cations by a divalent cation and a water molecule energetically unfavorable. It is also suggested that the inter-channel diffusion via the $T_{10}O_{20}$ windows of the channel walls may be the limiting factor for ion exchange applications in the natrolite group materials. Accordingly, superhydration and the associated channel expansion in natrolite at high pressure create a means for modifying both the nanopore geometry and chemistry within and provide novel and unprecedented applications for these small-pore zeolites.

The rest-lattice dimensions of the microporous materials are measured at standard temperature and pressure ("STP") conditions. For the purposes of the present invention STP conditions are defined as 300 °K (0 degrees Celsius) and 1 atmosphere pressure. Under increased pressure, the rest-lattice dimensions are altered and temporary lattice-enlarging structural distortions occur over specific pressure ranges for different types of microporous materials.

EXAMPLES

The experiments were conducted in a modified Merrill-Bassett Diamond Anvil Cell (DAC). A powder sample was placed in a 200 μm hole drilled in a steel gasket along with a few small ruby chips (to determine the hydrostatic pressure) and a pressure transmission fluid of water or methanol, ethanol and water in a ratio of approximately 16:3:1 by volume. (For example, in one series of tests, a 1 molar $Cd(C_2H_3O_2)_2$ aqueous solution mixed with methanol:ethanol:water in a ratio of 16:3:1 was used.) This fluid mixture is known to remain hydrostatic up to at least 10 GPa. The pressure induced swelling was observed only when water was present in the pressure transmission fluid. Water penetrates via the pores into Li- and Zn-exchanged zeolite A and expands the unit cell volume in an isotropic fashion. Non-penetrating fluids such as Fluorinert (trademark) (FC-75) and silicone oil did not show this effect. Also, transmission fluid containing only alcohols did not show this effect.

The Diamond Anvil Cell (DAC) was used at the X7A beamline of the National Synchrotron Light Source (NSLS) at Brookhaven National Laboratory (BNL). The primary white beam from the bending magnet was focused in the horizontal plane by a triangular, asymmetrically cut Si (220) monochromator bent to cylindrical curvature by applying a load to the crystal tip, affording micro-focused (~200 μm) monochromatic radiation of ~0.7 Å. A tungsten wire crosshair was positioned at the center of the goniometer circle and subsequently the position of the incident beam was adjusted to the crosshair. A gas-proportional position-sensitive detector (PSD) was stepped in 0.25° intervals over the angular range of 3–35° with counting times of 90–150 s per step. The wavelength of the incident beam (0.7054(1) Å for the natrolite run and 0.6942(1) Å for all other measurements), PSD zero channel and PSD degrees/channel were determined from a $CeO_2$ standard (SRM 674).

Powdered samples of the mineral natrolite (from Dutoitspan, South Africa, European Powder Metallurgy Association (EPMA): $Na_{16}Al_{16}Si_{24}O_{80}.16H_2O$), mesolite (Poona, India, EPMA: $Na_{4.8}Ca_{5.1}Al_{15.4}Si_{24.0}O_{80}.21.3H_2O$), scolecite (Nasik, India, EPMA: $Ca_{8.1}Al_{15.7}Si_{24.0}O_{80}.24H_2O$), and a synthetic gallosilicate analogue of natrolite (ICP, EPMA: $K_{16}Ga_{16}Si_{24}O_{80}.12H_2O$), were, in turn, loaded into the DAC at ambient pressure and room temperature along with a few small ruby chips. The DAC is based on a modified Merrill-Bassett design and employs two diamonds with 0.5 mm diameter culets on tungsten-carbide supports. The X-rays are admitted by a 0.5 mm diameter circular aperture, and the exit beam leaves via a 0.5×3.0 mm rectangular tapered slit, oriented perpendicular to the horizontal plane of the diffractometer. The sample chamber is a 200 or 350 μm hole formed in the center of a 300 μm thick Inconel gasket, pre-indented to 100 μm thickness before drilling. A mixture of methanol:ethanol:water was used as a pressure transmission fluid.

The pressure at the sample was measured by detecting the shift in the R1 emission line of the included ruby chips. No evidence of nonhydrostatic conditions or pressure anisotropy was detected during the experiments, and the instrumental errors on the pressure measurements ranged between about 0.05 to 0.1 GPa. Typically, the sample was equilibrated for about 15 min at each measured pressure. The DAC was then placed at the second axis of the diffractometer, and the sample position was adjusted using the pre-centered microscope. After the diffraction data measurement, the sample pressure was raised by 0.5~1.0 GPa increments before subsequent data measurements up to 5 GPa. Several pressure points were chosen for diffraction data measurements during pressure release. For natrolite, mesolite and the gallosilicate natrolite, there was no evidence of stress-induced peak broadening or pressure-driven amorphization and the recovered sample maintained its original white color and crystallinity. For scolecite, the experiment was repeated 5 times, and in all cases the measured diffraction data showed progressive broadening of the peaks at higher pressures up to 5 GPa.

Unit cell parameters were determined by whole pattern fitting using the Le Bail method, which extracts structure factors from powder diffraction data by iterating full pattern profile fitting. The diffraction peaks were modeled by varying only a half-width parameter in the pseudo-Voigt profile function. Bulk moduli were calculated by fitting the Murnaghan Equation of State to the normalized volumes ($V/V_0 = [1+B' P/B_0]^{-1/B'}$, where $B'=(\partial B/\partial P)_{P=0}=4$). For the data collected on natrolite, Rietveld structure refinements were performed using the General Structure Analysis System (GSAS) suite of programs. The starting framework model at each pressure point was constructed from Distant Least Squares (DLS)-minimization, which also provided constraints during the refinement processes. Difference Fourier maps were generated, and sodium and oxygen atoms were used to model the extra-framework species $Na^+$ and water molecules, respectively. Refinements of the fractional site occupancies indicated that these atoms fully occupy the extra-framework sites and were subsequently fixed to unity. An overall isotropic displacement parameter was used for the framework atoms; another was used for the non-framework oxygens and cations. Selected refinement results are listed in Tables 1 and 2.

Example 1

Natrolite

Figure 4:
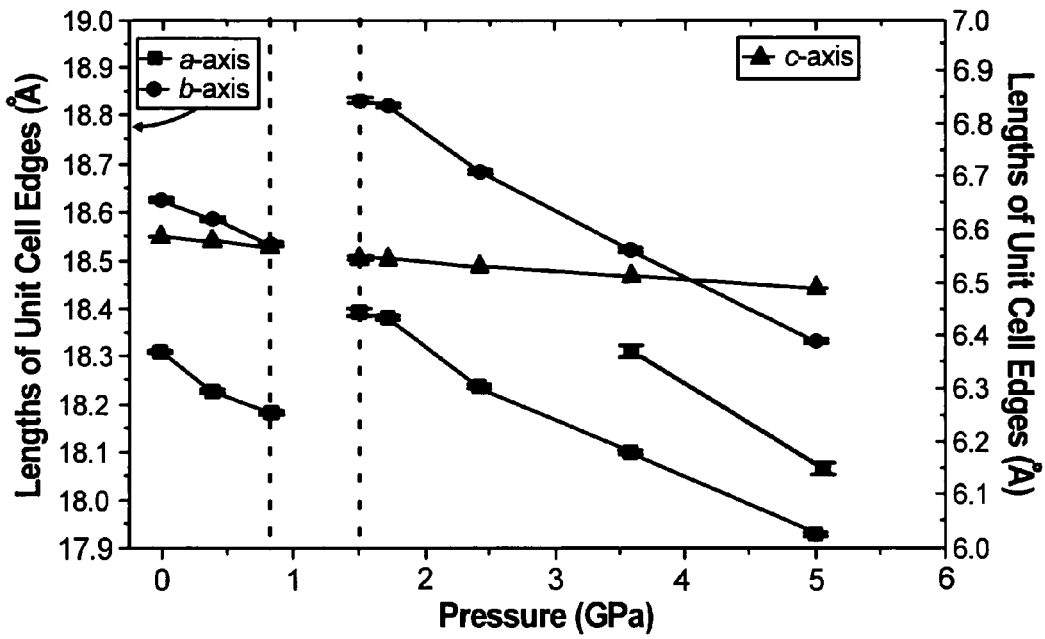
FIG. 4 is a graph showing the changes in the unit cell edge lengths (Å) of natrolite as a function of pressure.

For this example, the pressure-induced volume expansion of natrolite (sodium aluminosilicate natrolite, $Na_{16}Al_{16}Si_{24}O_{80}.16H_2O$) was evaluated. The evolution of the unit cell parameters of natrolite is shown in FIG. 4.

Figure 5:
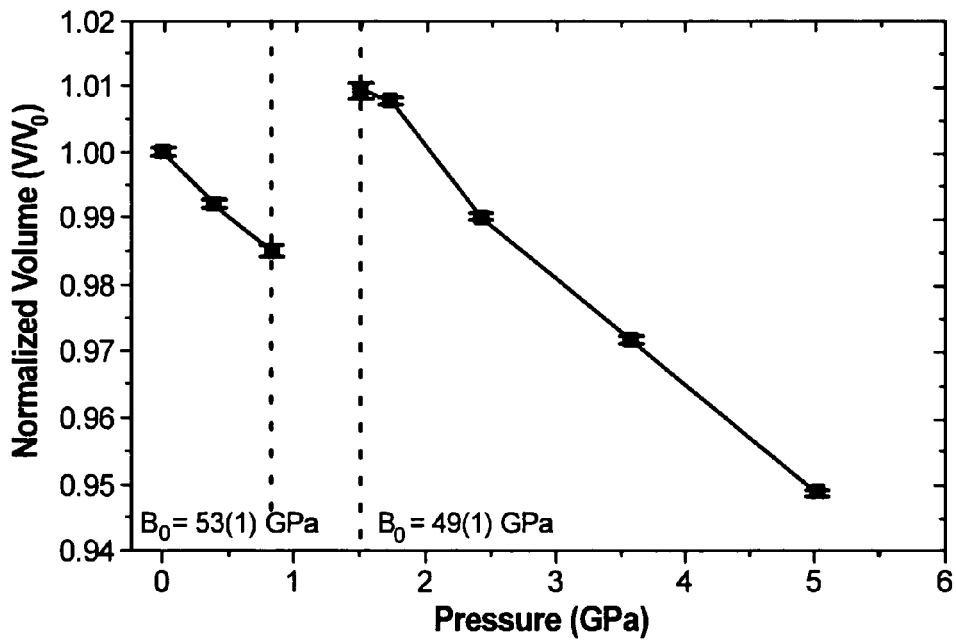
FIG. 5 is a graph showing the pressure dependence of the unit cell volume of natrolite, normalized to their ambient pressure value.
Figures 6, 7:
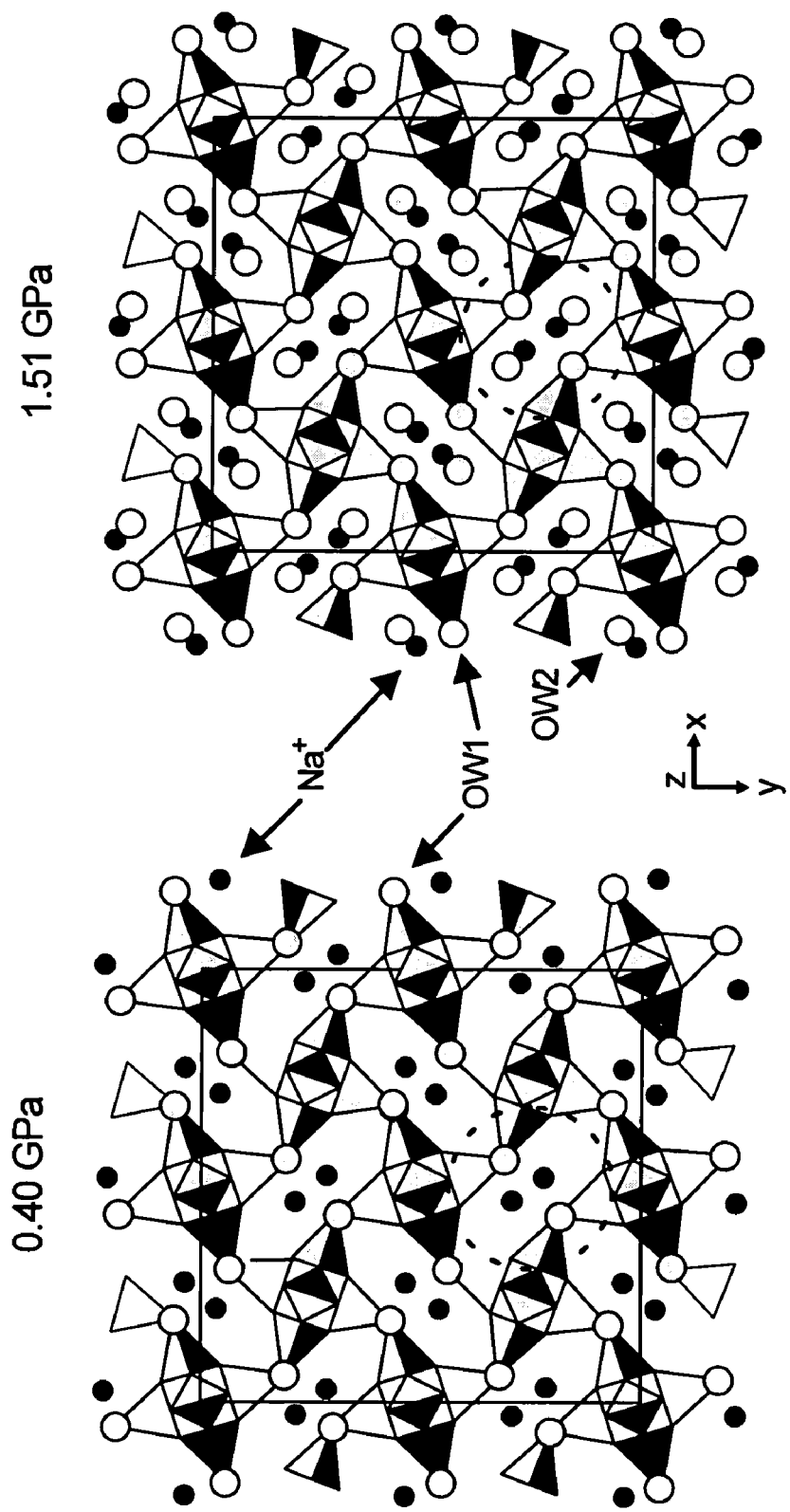
FIG. 6 is a polyhedral representations of natrolite at 0.40 GPa viewed along [001], the chain/channel axis
FIG. 7 is a polyhedral representations of natrolite at 1.51 GPa viewed along [001], the chain/channel axis

Between 0.8 and 1.5 GPa, the pressure-induced swelling is caused by the expansion of the unit cell along the a- and b-unit cell axes whereas the c-axis shows the expected contraction behavior with pressure throughout the volume expansion period. This two-dimensional swelling suggests that the rotation of the chains along the c-axis and subsequent expansion of the channels in the (001) plane is responsible for the observed volume increase. The calculated bulk modulus of the large-volume natrolite ($B_0$=49(1) GPa) is slightly smaller than that of the normal natrolite ($B_0$=53(1) GPa), illustrating increased compressibility for this high-water-content phase. FIG. 5 shows changes in the unit cell edge lengths (measured in Angstroms, Å) of natrolite as a function of pressure. The estimated standard deviations ("ESD's") are multiplied by three at each point.

representations in FIGS. 6 and 7 are viewed along [001], the chain/channel axis. The large-light circles represent water molecules and the small-dark circles represent sodium cations. Before the volume expansion, the Na atom maintains its coordination of two water oxygens and four framework oxygens in a distorted trigonal prism. Considering only the extra-framework species, the water molecules and the sodium cations bond to form a zigzag chain along the c-axis. After the volume expansion at 1.5 GPa, an additional fully occupied water site (OW2) appears along the channel, increasing the crystal water content to 32 $H_2O$ per unit cell. This new site has been proposed to be half-filled with water molecules in paranatrolite (24 $H_2O$ per unit cell), which leads to an anomalous increase in the water mobility observed in NMR and other spectroscopic measurements.

TABLE 1

Final refined atomic coordinates for natrolite as a function of pressure[a]

| SPACE GROUP | | 0.40 GPa Fdd2 | 0.84 GPa Fdd2 | 1.51 GPa Fdd2 | 1.72 GPa Fdd2 | 2.42 GPa Fdd2 | 3.58 GPa Fdd2 | 5.01 GPa Fdd2 |
|---|---|---|---|---|---|---|---|---|
| DLS R-value[b] | | 0.0029 | 0.0029 | 0.0028 | 0.0028 | 0.0031 | 0.0035 | 0.0040 |
| $_wR_p$ (%), $R_p$ (%), $\chi^2$ | | 4.5, 2.9, 1.3 | 5.6, 3.9, 1.0 | 5.2, 3.4, 1.2 | 4.1, 2.6, 1.1 | 6.7, 3.4, 3.6 | 4.6, 3.0, 1.5 | 4.5, 2.9, 1.4 |
| cell length (Å) | a | 18.226(2) | 18.180(4) | 18.390(6) | 18.378(3) | 18.233(3) | 18.097(2) | 17.924(2) |
| | b | 18.583(2) | 18.531(4) | 18.829(6) | 18.818(3) | 18.679(3) | 18.518(2) | 18.325(2) |
| | c | 6.579(1) | 6.566(2) | 6.547(2) | 6.545(1) | 6.530(1) | 6.512(1) | 6.487(1) |
| Si(1) 8a | x | 0 | 0 | 0 | 0 | 0 | 0 | 0 |
| Si(2) 16b | x | 0.1493(1) | 0.1491(1) | 0.1536(1) | 0.1534(1) | 0.1505(4) | 0.1510(2) | 0.1507(2) |
| | y | 0.2168(1) | 0.2177(1) | 0.2106(1) | 0.2107(1) | 0.2134(4) | 0.2128(2) | 0.2128(2) |
| | z | 0.6180(2) | 0.6177(2) | 0.6172(2) | 0.6172(1) | 0.6173(9) | 0.6175(3) | 0.6166(3) |
| Al 16b | x | 0.0338(1) | 0.0331(1) | 0.0400(1) | 0.0399(1) | 0.0376(4) | 0.0375(2) | 0.0368(2) |
| | y | 0.0975(1) | 0.0977(1) | 0.0929(1) | 0.0930(1) | 0.0952(4) | 0.0957(2) | 0.0963(2) |
| | z | 0.6095(2) | 0.6097(2) | 0.6099(2) | 0.6099(1) | 0.6085(9) | 0.6098(3) | 0.6103(3) |
| O(1) 16b | x | 0.0170(4) | 0.0131(3) | 0.0400(3) | 0.0400(2) | 0.0383(8) | 0.0404(4) | 0.0435(3) |
| | y | 0.0695(1) | 0.0705(1) | 0.0588(2) | 0.0588(1) | 0.0605(5) | 0.0602(3) | 0.0590(2) |
| | z | 0.8592(2) | 0.8589(2) | 0.8586(2) | 0.8585(1) | 0.8577(9) | 0.8587(4) | 0.8579(3) |
| O(2) 16b | x | 0.0662(1) | 0.0660(1) | 0.0711(1) | 0.0708(1) | 0.0668(4) | 0.0659(2) | 0.0641(2) |
| | y | 0.1861(1) | 0.1864(1) | 0.1807(1) | 0.1809(1) | 0.1844(4) | 0.1860(2) | 0.1879(2) |
| | z | 0.6080(3) | 0.6078(3) | 0.6079(3) | 0.6079(2) | 0.6090(16) | 0.6077(6) | 0.6072(6) |
| O(3) 16b | x | 0.0991(1) | 0.0995(1) | 0.0968(1) | 0.0969(1) | 0.0969(6) | 0.0963(3) | 0.0946(3) |
| | y | 0.0404(2) | 0.0398(2) | 0.0408(1) | 0.0410(1) | 0.0444(4) | 0.0450(2) | 0.0467(2) |
| | z | 0.4997(9) | 0.5072(7) | 0.4565(6) | 0.4564(3) | 0.4556(19) | 0.4525(8) | 0.4439(7) |
| O(4) 16b | x | 0.2018(2) | 0.2025(2) | 0.2011(1) | 0.2009(1) | 0.1980(4) | 0.1967(2) | 0.1942(2) |
| | y | 0.1569(1) | 0.1568(1) | 0.1596(1) | 0.1596(1) | 0.1606(6) | 0.1597(3) | 0.1600(3) |
| | z | 0.7219(9) | 0.7143(7) | 0.7650(6) | 0.7652(3) | 0.7634(18) | 0.7686(8) | 0.7772(7) |
| O(5) 16b | x | 0.1791(1) | 0.1781(1) | 0.1898(2) | 0.1897(1) | 0.1878(5) | 0.1885(3) | 0.1900(2) |
| | y | 0.2335(4) | 0.2374(3) | 0.2111(3) | 0.2111(2) | 0.2126(7) | 0.2105(4) | 0.2072(3) |
| | z | 0.3909(2) | 0.3912(2) | 0.3917(2) | 0.3917(1) | 0.3915(9) | 0.3917(4) | 0.3922(3) |
| Na 16b | x | 0.220(1) | 0.221(1) | 0.224(1) | 0.224(1) | 0.217(1) | 0.228(2) | 0.225(1) |
| | y | 0.035(1) | 0.036(1) | 0.028(1) | 0.029(1) | 0.029(1) | 0.024(1) | 0.025(1) |
| | z | 0.623(2) | 0.638(4) | 0.629(5) | 0.599(4) | 0.557(4) | 0.615(3) | 0.623(3) |
| OW1 16b | x | 0.059(1) | 0.054(2) | 0.055(2) | 0.055(2) | 0.065(2) | 0.061(1) | 0.060(1) |
| | y | 0.190(1) | 0.184(2) | 0.181(2) | 0.180(1) | 0.178(2) | 0.182(1) | 0.186(1) |
| | z | 0.110(4) | 0.139(8) | 0.12(1) | 0.107(8) | 0.113(9) | 0.113(7) | 0.117(6) |
| OW2 16b | x | | | 0.184(2) | 0.180(2) | 0.190(1) | 0.180(1) | 0.181(1) |
| | y | | | 0.071(2) | 0.066(1) | 0.067(2) | 0.070(1) | 0.081(1) |
| | z | | | 0.110(6) | 0.086(5) | 0.054(6) | 0.110(4) | 0.088(4) |

[a]Estimated standard deviations (ESD's) are in parentheses. Fixed isotropic displacement parameters, $U_{iso}$ (Å$^2$), were used for all models (0.017 and 0.022 for framework and extra-framework elements, respectively). All sites are fully occupied.
[b]Generated from starting framework models. In addition, unlike the sodium-water chains in the low-pressure phase below 0.8 GPa, The changes in the crystal structure accompanying the pressure-induced swelling were investigated by performing Rietveld refinements using the framework geometrical restraints and the diffraction data collected in the pressure range examined, see Table 1 for details. The two structural models for the phases before and after the volume expansion are shown in FIGS. 6 and 7. FIG. 6 is a polyhedral representation of natrolite at 0.40 GPa and FIG. 7 is a polyhedral representation of natrolite at 1.51 GPa. The the superhydration at the OW2 site generates a helical nanotube of hydrogen-bonded water molecules along the c-axis. The structure of the non-framework species found in natrolite viewed perspective along the c-axis is shown 0.40 GPa at 1.51 GPa in FIGS. 8 and 9, respectively. Of special note is the formation of the hydrogen-bonded water nanotube at 1.51 GPa. The large-light circles represent water molecules and the small-dark circles represent sodium cations. The straight lines define unit cells and the short bars define hydrogen bonds.

During the superhydration occurring between 0.8 and 1.5 GPa, peak splittings in the powder diffraction pattern were observed at 1.25 GPa. This indicated that at this pressure a pseudo-orthorhombic paranatrolite (with disordered water sublattice) or its mixture with the superhydrated orthorhombic natrolite was present. A second set of experiments was performed to investigate more carefully the phases present during superhydration. Several pressure points between 0.8 and 2.0 GPa were chosen to collect diffraction patterns. The measured data were consistent with the existence of two phases during the superhydration and volume expansion. The new phase has a larger unit cell length for the a- and b-axes (~18.9 Å and ~19.1 Å, respectively) and a smaller c-axis (~6.5 Å) than those of the normal and superhydrated natrolite and shows peak splittings suggesting a pseudo-orthorhombic distortion. This is consistent with the presence of paranatrolite with 24 $H_2O$ per unit cell before superhydration increases the water content to 32. In both runs, diffraction data on the recovered sample underlined the reversibility of the system, with the unit cell parameters being the same as those under ambient conditions (within 3).

Figure 10:
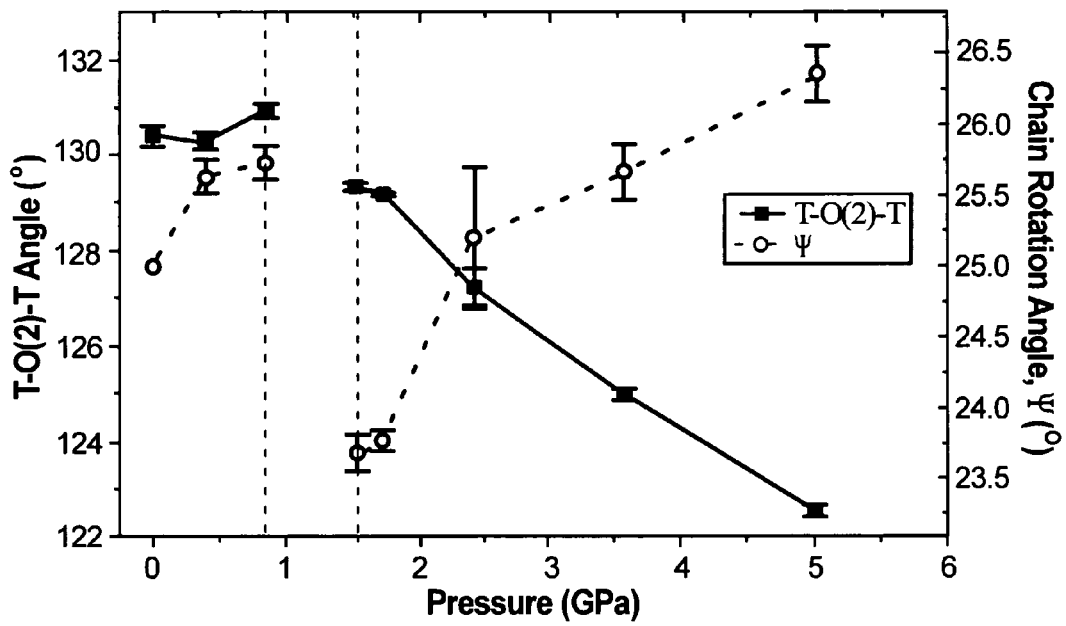
FIG. 10 is a graph showing the changes in T-O2-T bond angle and overall chain rotation angle of natrolite as a function of pressure.

The changes in framework geometry were monitored using the T-O-T bond angles within and between the chains. FIG. 10 shows changes in T-O2-T bond angle and overall chain rotation angle of natrolite as a function of pressure. The T-O-T angles within the chain do not follow any systematic changes whereas the bridging T-O2-T angle between the chains shows small changes before, and a continuous contraction after the superhydration, respectively. At the same time, the overall chain rotation angle, $\psi$, increases initially up to 25.7° at 0.8 GPa, then drops to 23.7° during superhydration, and increases back up at 5.0 GPa. This indicates that superhydration is coupled to the relaxation of the overall distortion of the framework by expanding the pore space perpendicular to the channel.

Example 2

Mesolite

Figure 11:
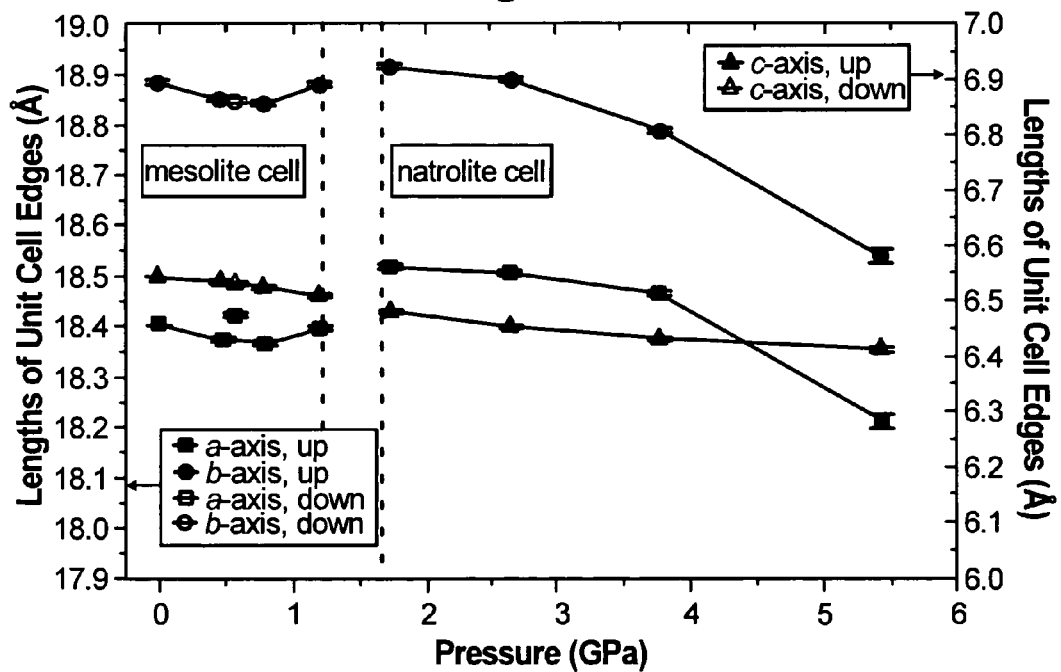
FIG. 11 is a graph showing the lengths of unit cell edges versus pressure for a mesolite cell and a natrolite cell.
Figure 12:
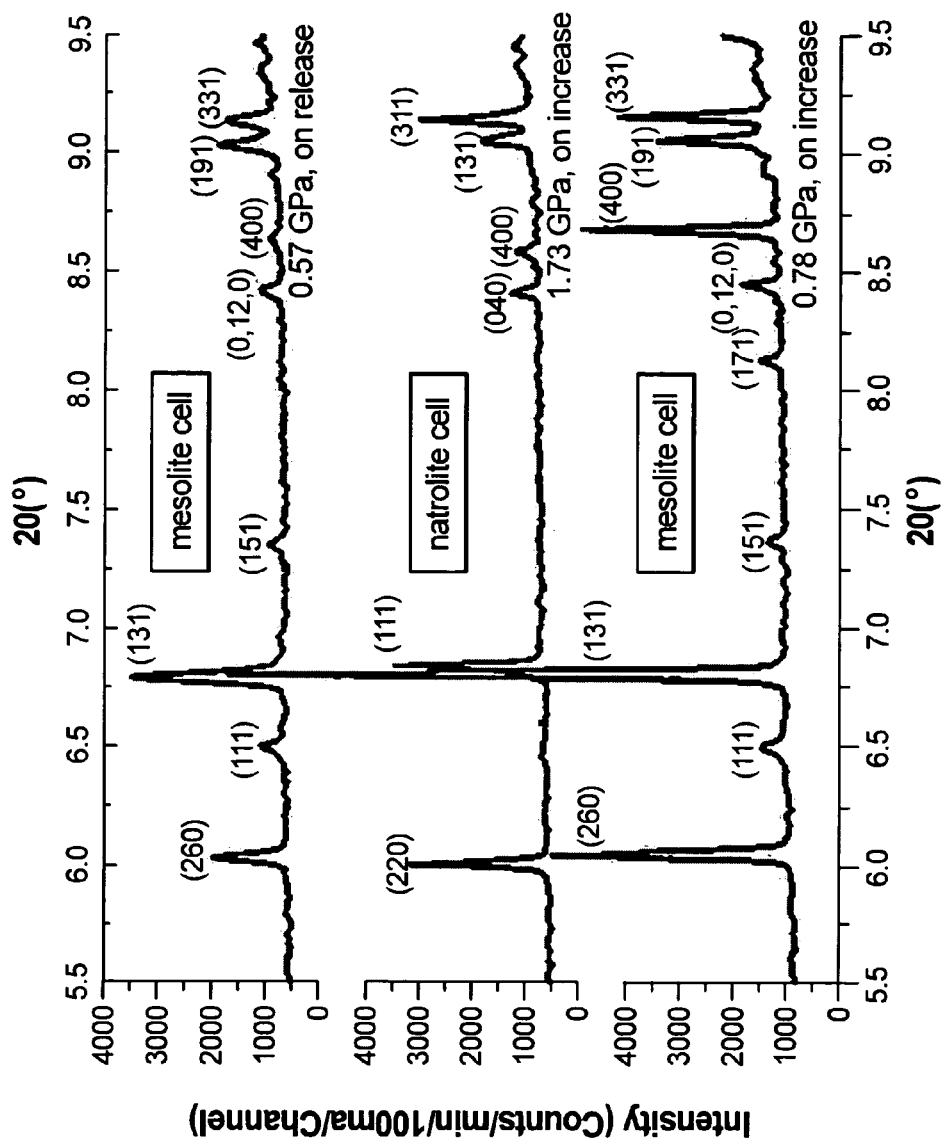
FIG. 12 is a graph showing three representative powder diffraction patterns for mesolite as a function of pressure.

This example evaluated the pressure-induced volume expansion of mesolite, ($Na_{5.33}Ca_{5.33}Al_{16}Si_{24}O_{80} \cdot 21.33\ H_2O$). The changes of the unit cell parameters of mesolite are displayed as a function of pressure in FIG. 11, with three representative powder diffraction patterns shown in FIG. 12. FIG. 11 shows that mesolite captures specified materials between about 1.2 and 1.75 GPa. Pressure-induced swelling in mesolite reduces the periodicity of one of its axes (b-axis) so that its structure is similar to the structure of natrolite. The high-pressure phase of mesolite above 1.73 GPa is characterized by a two-dimensionally expanded unit cell along the a- and b-axes and the absence of superlattice reflections with k 3n. The latter is an indication of an order/disorder transition in mesolite and was observed during its dehydration process where the well-defined natrolite and scolecite layers become indistinguishable upon the loss of the Ca-coordinating water and subsequent disordering of Na and Ca cations throughout the neighboring channels.

Figure 13:
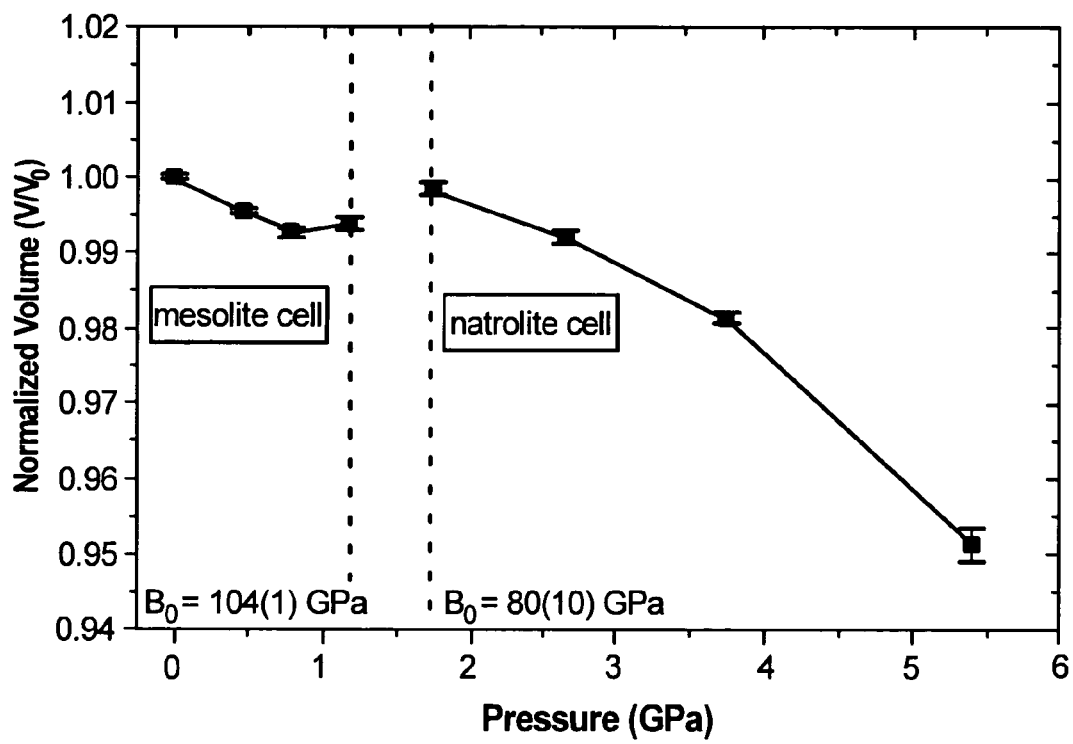
FIG. 13 is a graph showing the normalized volume versus pressure for a mesolite cell and a natrolite cell.

This is the first observation of a pressure-induced cation disordering in zeolites: it is rather remarkable since in this study a hydration is probably the driving force for the cation disordering rather than the more commonly observed dehydration. Unlike the evolution of the powder diffraction pattern measured in natrolite, there is no manifestation of an intermediate phase between the normal (ordered) and expanded (disordered) phases. Instead, the a- and b-unit cell lengths increase slightly at 1.19 GPa before the order-disorder transition sets in. In mesolite, the Ca channels already contain 50% more water molecules when compared to the Na channels. As a result, the overall volume increase is only 0.5% compared to 2.5% in natrolite. FIG. 13 shows a comparison of the normalized volume of mesolite and natrolite as a function of pressure. When the pressure was released, the mesolite superlattice reflections were recovered with comparable d-spacings to those before superhydration. The calculated bulk-modulus of the disordered, sublattice phase ($B_0$=80(10) GPa) is smaller than the one of the superlattice phase before the volume expansion ($B_0$=104(1) GPa) (see FIG. 13).

The high-pressure powder diffraction data measured on mesolite sample were not of sufficient quality to locate the new water sites through Rietveld structure refinements.

Example 3

Scolecite

Figure 14:
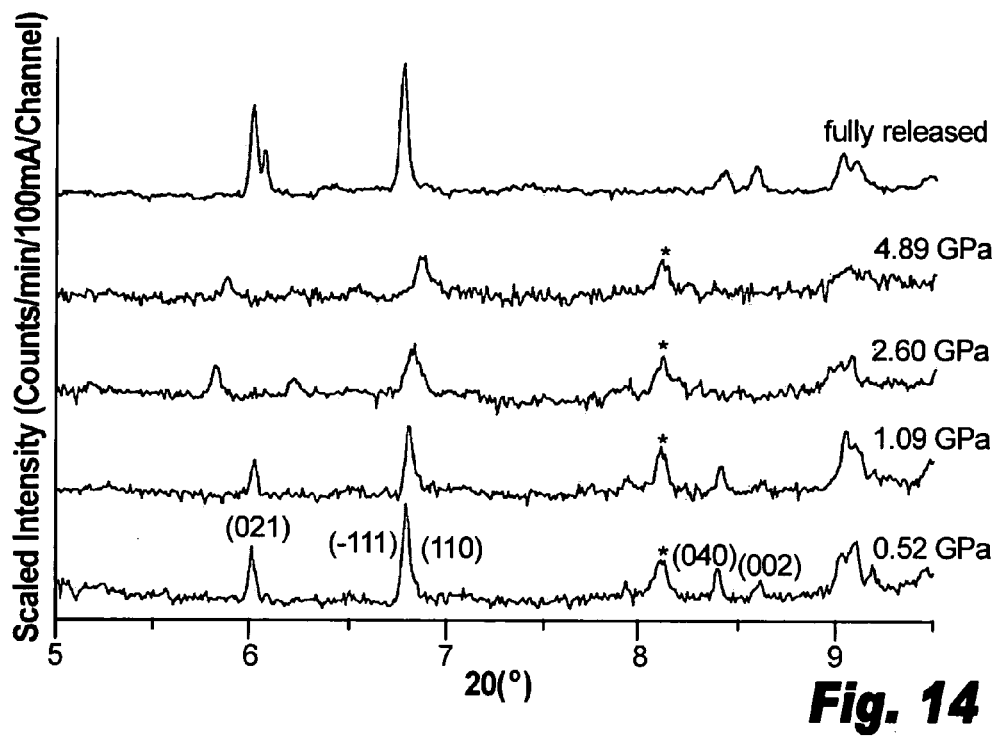
FIG. 14 is a graph showing powder diffraction patterns of scolecite as a function of pressure.

In this example, the pressure-induced volume expansion of scolecite, ($Ca_8Al_{16}Si_{24}O_{80} \cdot 24H_2O$), was evaluated. Scolecite capture specified materials at a pressure of from about 2 to about 3 GPa. The high-pressure behavior up to 5 GPa of scolecite, the Ca-end-member of natrolite, does not resemble that of natrolite and mesolite under the same hydrostatic conditions. Powder diffraction data of scolecite from five separate high-pressure runs all show progressive peak-broadening along with decreased peak intensities. This effect becomes notable above 2 GPa where, in some cases, a volume expansion is observed by diffraction peaks shifted to lower 2θ values. FIG. 14 shows the broadening and reduction in intensity of the diffraction peaks above 2 GPa. Pressure-induced amorphization has often been noticed while exploring the high-pressure crystal chemistry of zeolites where quasi-hydrostatic solid pressure media such as pyrophyllite or KBr are used which are known to exert shear stress on the sample. The loss of long-range order in zeolites under moderate hydrostatic pressures, especially here when pore-penetrating liquids are used as a pressure-transmission medium, is therefore an uncommon example of a hydrostatic pressure-induced amorphization effect. When the pressure was released, the crystallinity of the scolecite phase was regained and the overall intensities of the peaks after decompression were close to those before compression.

The peaks from the fully-released sample have similar d-spacings as those from the starting material ($d_{(021)}$=6.61 (1) Å after decompression, $d_{(021)}$=6.62(1) Å before compression). It was noted that the peak measured at d=6.55(3) Å (just after the (021) in the fully released sample) was not observed in the other runs. It may arise from a mixture of two phases after decompression or indicate a splitting of (021) at the higher pressures to which this sample was subjected. Further analysis of the data was not possible due to the poor peak resolution and peak-to-background ratio for this pseudo-orthorhombic analogue.

Example 4

Potassium Gallosilicate Analogue of Natrolite

Figure 15:
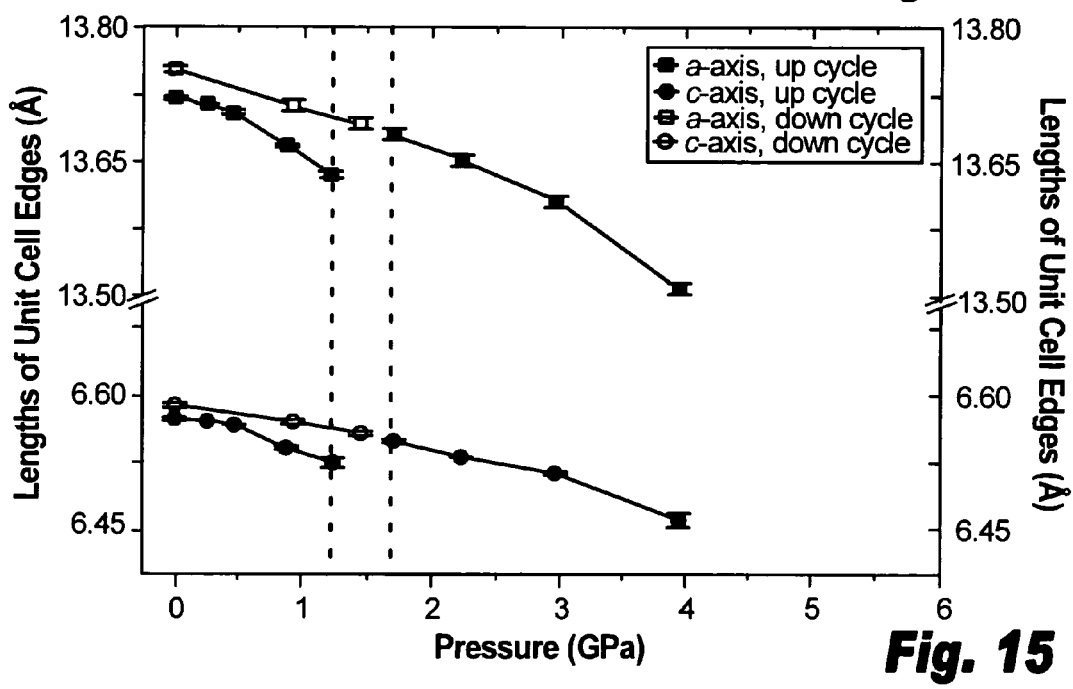
FIG. 15 is a graph showing changes in the unit cell edge lengths (Å) of the potassium gallosilicate analogue of natrolite as a function of pressure.
Figure 16:
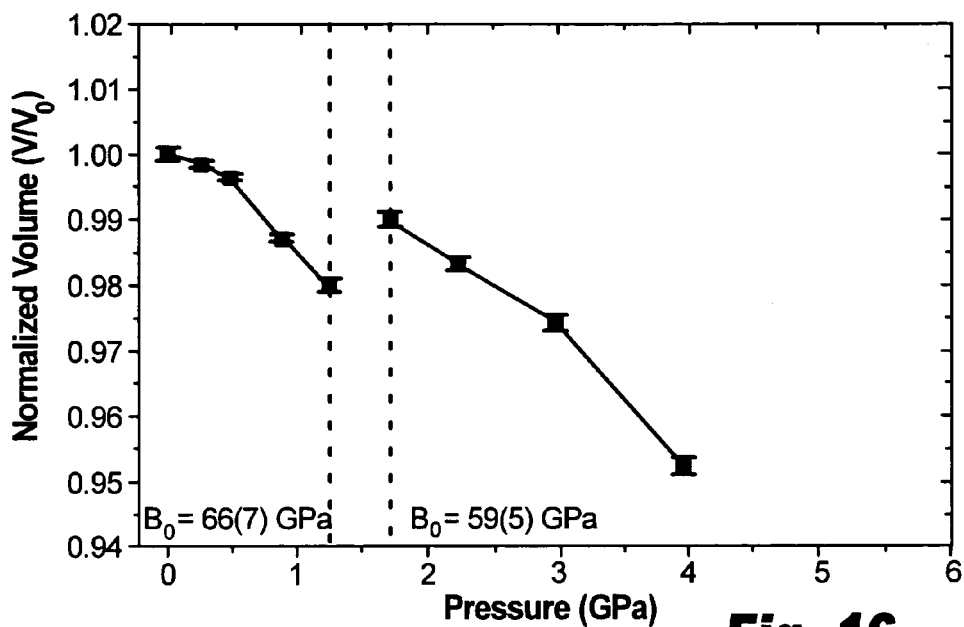
FIG. 16 is a graph showing the pressure dependence of the unit cell volume of the gallosilicate natrolite, normalized to their ambient pressure value.

This example evaluated the pressure-induced volume expansion of the potassium gallosilicate analogue of natrolite, $K_{16}Ga_{16}Si_{24}O_{80} \cdot 12H_2O$ or K—GaSi-NAT. The changes of the unit cell parameters of the potassium gallosilicate natrolite as a function of pressure are shown in FIG. 15. The volume expansion occurs between about 1 and about 2 GPa, with about 1.0% volume expansion occurring between about 1.24 and about 1.71 GPa. FIG. 16 shows pressure dependence of the unit cell volume of the gallosilicate natrolite, normalized to their ambient pressure value. The manner in which this expansion takes place in this material is, however, different to that observed in natrolite and mesolite: it shows a three-dimensional swelling. The c-axis, along which the rigid $T_5O_{10}$ tetrahedral building units join to form the fibrous chain, expands by about 0.4% in the gallosilicate natrolite whereas it contracts in natrolite and mesolite upon compression. More strikingly, when releasing pressure the larger-volume phase, probably superhydrated, is stabilized. The unit cell volume of the recovered sample is 0.7% larger than the unit cell volume of the sample before compression.

In order to follow the changes in the unit cell volume as a function of time, sets of diffraction data were collected 3 and 8 days after pressure release. There was no indication of a further volume contraction and the cell constants were the same as those measured right after ending the pressure cycle (within 2σ). The overall intensity of the peaks decreases slightly as pressure increases. The shape of the peaks, however, does not show any degradation, suggesting pressure-induced amorphization does not occur in this material under hydrostatic conditions up to 4 GPa. Compressibility of the expanded phase above 1.71 GPa ($B_0$=59(5) GPa) is slightly larger than that of the phase before the volume expansion ($B_0$=66(7) GPa), consistent with the trend found in natrolite and mesolite (see FIG. 16). Further structure refinements using these data were not successful due to the significant overlap of the reflections with the backgrounds from the gasket material above 18° in 2θ.

Example 5

Zn-Containing Form of Linde A ($Zn_6[Al_{12}Si_{12}O_{48}]$ $29H_2O$)

This example evaluated the pressure-induced volume expansion of the Zn-containing form of Linde A ($Zn_6$ $[Al_{12}Si_{12}O_{48}]$ $29H_2O$), which was produced through standard aqueous ion-exchange methods from a commercial sample of zeolite Na-A (Aldrich) using a 0.1 M solution of zinc nitrate at 80° C. Complete exchange was confirmed by Inductively-Coupled Plasmaspectrometer ("ICP") analysis, which gave a ratio of Na:Zn:Al of 0.2:5.9:12.0, and indicated over-exchange is not an issue. The observed lattice constant, 12.1218(5) Å, agrees well with the literature values from both powder, 12.12 Å, and single crystal data, 12.163(1) Å, indicative of a complete exchange of zinc for sodium. For the commercial sample of Na-A, ICP analysis gave a ratio of Na:Al of 11.9:12.0 and the measured lattice constant was 12.2904(6) Å. For the purposes of this example, the ~12.3 Å primitive cubic subcell for zeolite A was adequate.

Figure 17:
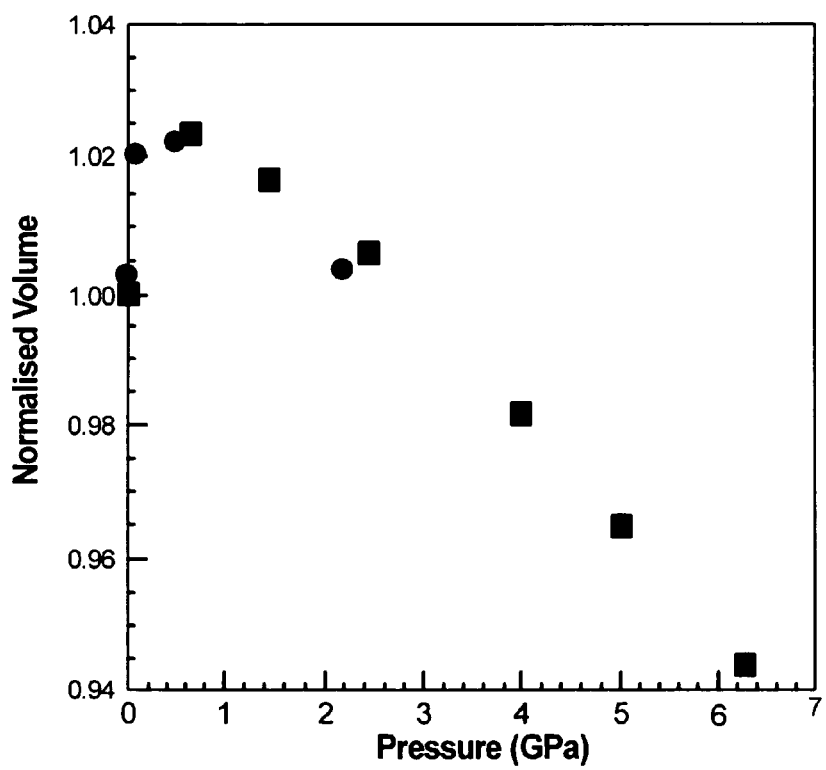
FIG. 17 is a graph showing the pressure dependence of the unit cell volume of the Zn-containing form of Linde A, $Zn_6[Al_{12}Si_{12}O_{48}]$ $29H_2O$ as a function of pressure.

The changes of the unit cell parameters of the Zn-containing form of Linde A as a function of pressure are shown in FIG. 17. The volume expansion occurs up to about 0.6 GPa and there is an unambiguous increase in the unit-cell volume with applied hydrostatic pressures up to about 0.6 GPa when the pressure-transmitting medium is alcohol/water (16:3:1 methanol/ethanol/water) or pure water, but not if the fluorocarbon ether FC-75 or silicone oil are used. The effect is as large as 2.25% at 0.5 GPa. This clearly implicates the uptake of extra water molecules into the pores during the PIE but, unlike natrolite, 4–6 the solid is fully hydrated at ambient pressure and does not contain any obvious structural voids to be filled by the additional fluid.

Above 0.6 GPa, the expansion gives way to the commonly observed decrease of cell volume with increasing pressure. This was found to be reversible; upon pressure release from 6.3 GPa the cell volume smoothly increased to 0.5 GPa, and then decreased with further pressure release. In order to prove that pressure is required for expansion, a sample of the same material was placed in a sealed capillary with a large amount of the same alcohol/water mixture. Even after 2 days, the volume of the solid did not change. In contrast, PIE was not observed for zeolite Na-A in the alcohol/water mixture or Ca-A in pure water. These cation forms have similar water contents (29 molecules per unit cell for Zn, 27 for Na and 28 for Ca), and Zn-A and Ca-A also have identical numbers of cations. If the effect is simply due to filling of the small amount of space that is still empty in the fully hydrated forms, all three zeolites should exhibit similar pressure behavior.

Example 6

Lithium Exchanged Linde A ($Li_{12}[Al_{12}Si_{12}O_{48}]$ $29H_2O$)

This example evaluated the pressure-induced volume expansion of the Lithium exchanged Linde A ($Li_{12}$ $[Al_{12}Si_{12}O_{48}]$ $29H_2O$). The Ca-exchanged form of zeolite A was produced in a similar manner as the Zn-containing form of Linde A. In this case, the exchange was not quite complete based on ICP analysis which gave a ratio of Na:Ca:Al of 1.2:4.5:12.0. Based on Na Magic Angle Spinning-Nuclear Magnetic Resonance ("MAS-NMR"), it is believed that the sodium content is correct as determined and the calcium content slightly higher than measured. The lattice constant at ambient pressure was 12.316(3) Å, which agrees well with the literature value of 12.305 Å.

Figure 18:
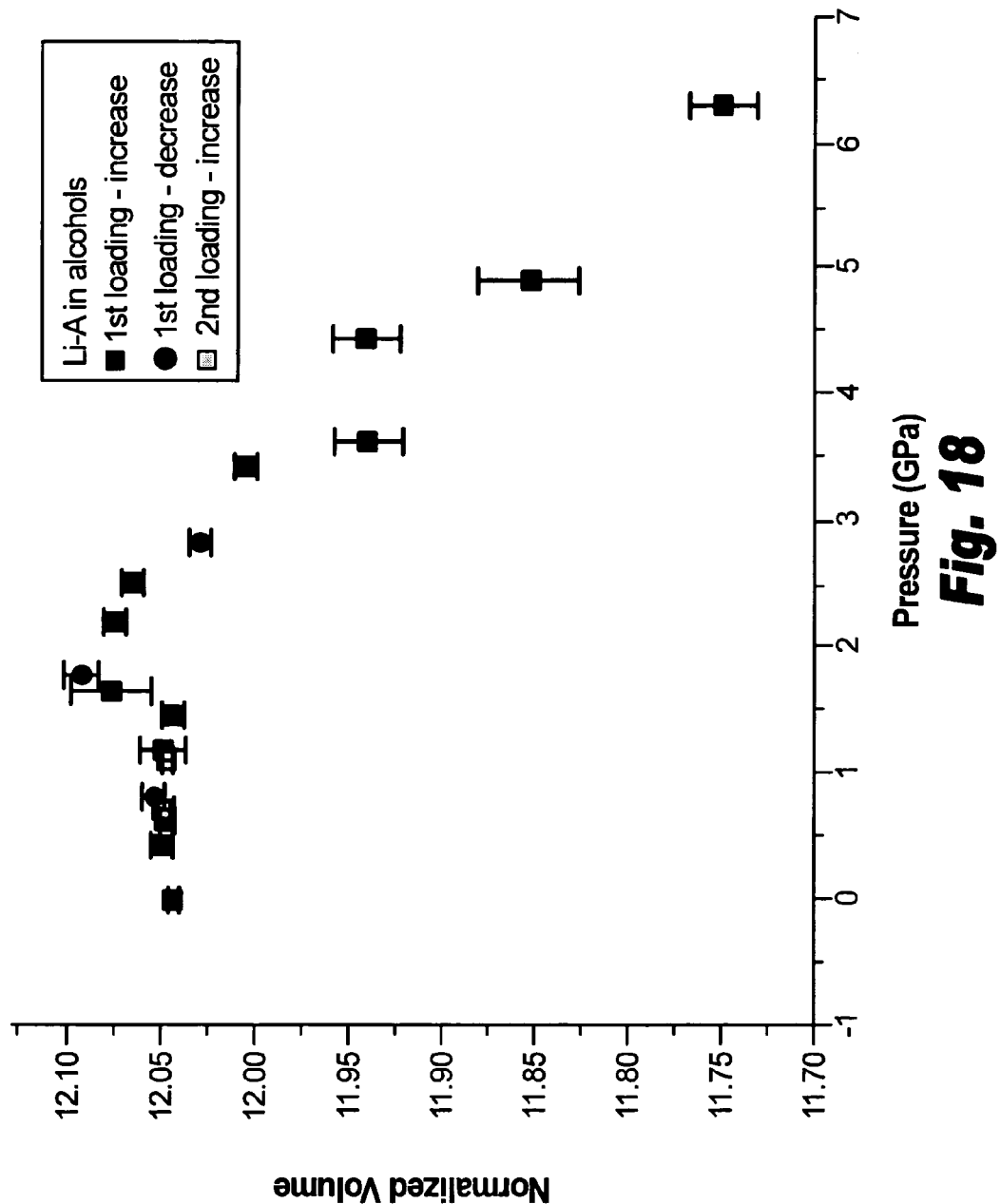
FIG. 18 is a graph showing the pressure dependence of the unit cell volume of the Lithium exchanged Linde A, $Li_{12}[Al_{12}Si_{12}O_{48}]$ $29H_2O$ as a function of pressure.

The changes of the unit cell parameters of the Lithium exchanged Linde A as a function of pressure are shown in FIG. 18. The volume expansion occurs between about 1.5 and about 2 GPa.

Example 7

Gallosilicate Analogue of Natrolite

Figure 19:
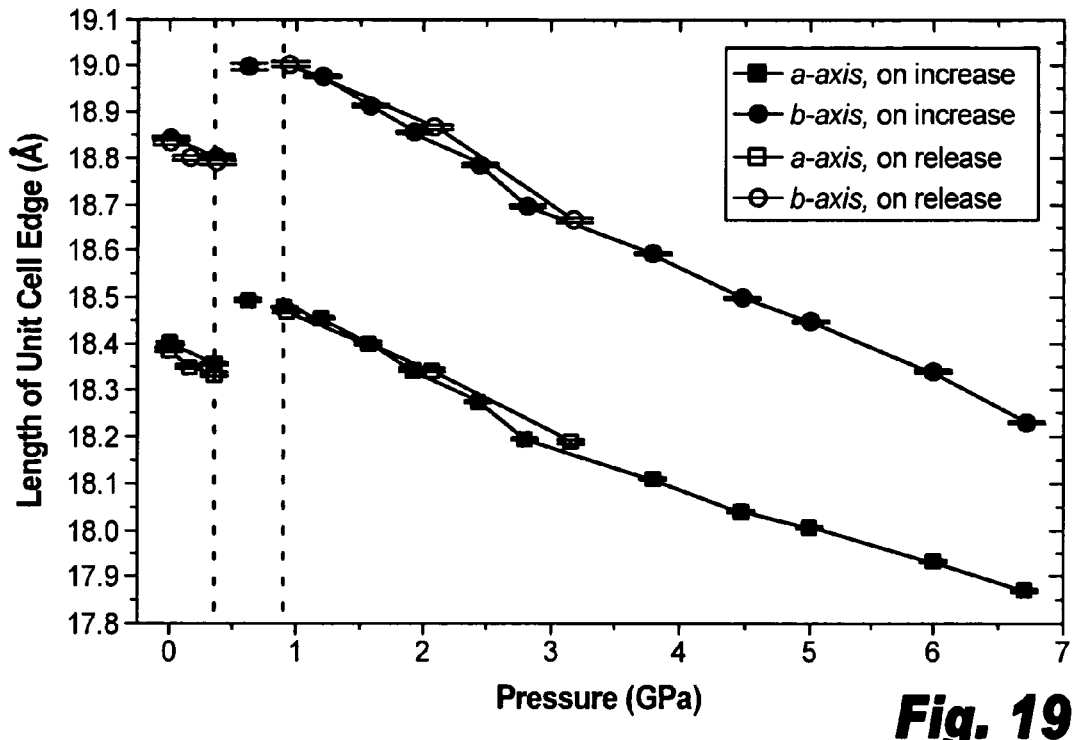
FIG. 19 is a graph showing changes in the unit cell edge lengths (Å) of the gallosilicate analogue of natrolite as a function of pressure for the a and b axes.
Figure 20:
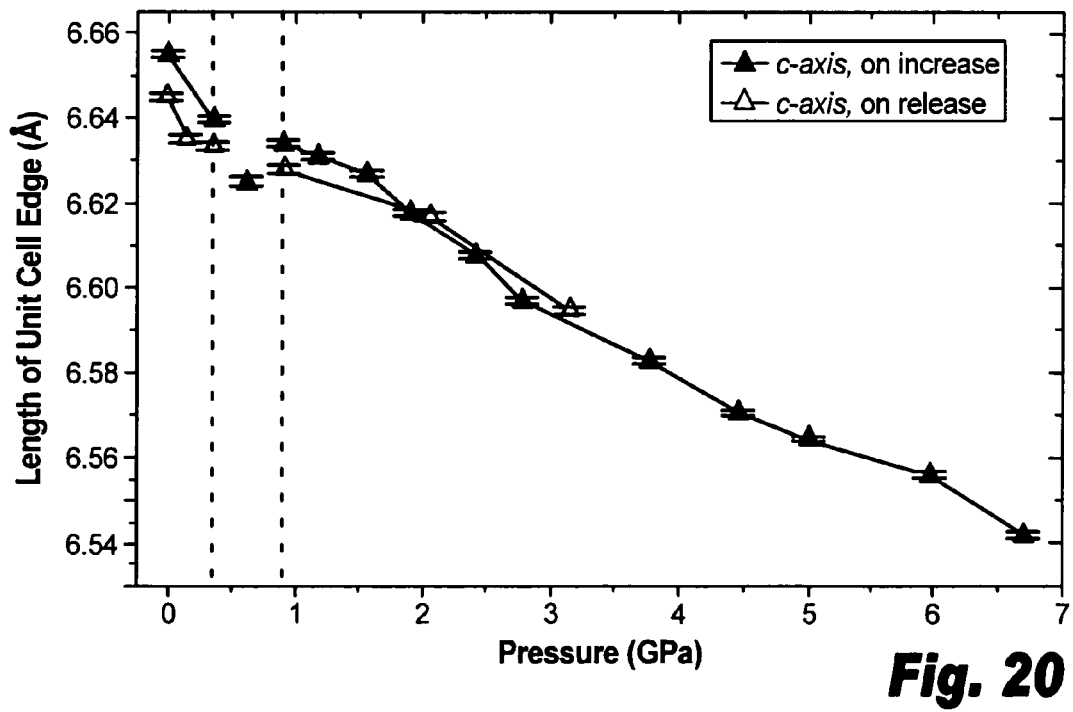
FIG. 20 is a graph showing changes in the unit cell edge length (Å) of the gallosilicate analogue of natrolite as a function of pressure for the c axis.
Figure 21:
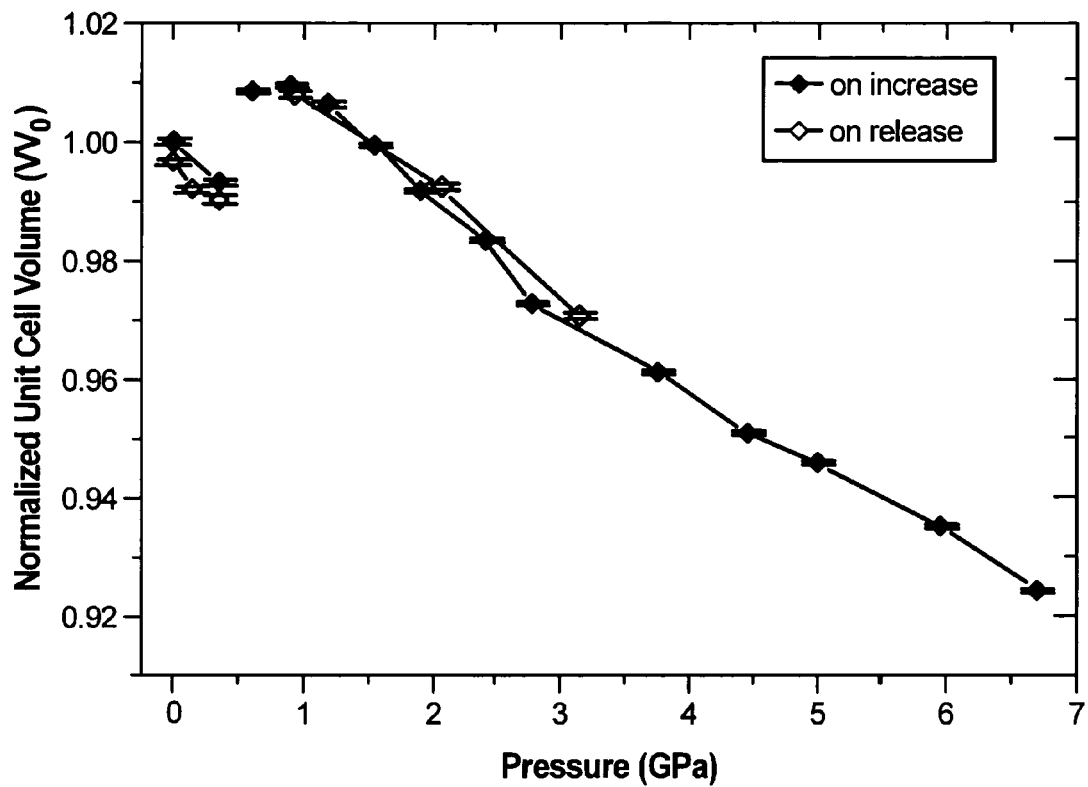
FIG. 21 is a graph showing the pressure dependence of the unit cell volume of the gallosilicate analogue of natrolite, normalized to their ambient pressure value.

For this example, the pressure-induced volume expansion of a gallosilicate analogue of natrolite, $Na_{16}Ga_{16}Si_{24}O_{80} \cdot 16H_2O$ (wherein gallium (Ga) was substituted for aluminum (Al)), was evaluated. The changes of the unit cell parameters of the gallosilicate natrolite analogue as a function of pressure are shown in FIGS. 19 and 20. The volume expansion occurs between about 0.2 and about 0.9 GPa, with about 2.1% volume expansion occurring between about 0.35 and about 0.6 GPa. FIG. 21 shows pressure dependence of the unit cell volume of the gallosilicate natrolite analogue, normalized to their ambient pressure value. The gallosilicate analogue expands at pressures which lower than natrolite.

Superhydration and Volume Expansion Under Pressure

The arrangement of non-framework cations and water molecules inside the natrolite channels before and after superhydration are depicted in FIGS. 8 and 9. The two-dimensional swelling between 0.84 and 1.51 GPa corresponds to a decrease in the ellipticity of the helical 8-ring channel by 6.7% (the ellipticity is defined by the ratio between the shortest to longest framework oxygen distances of the channel opening: the shortest O2—O2 distance across the channel increases from 4.70(1) to 4.94(1) Å upon superhydration). This is compatible with the changes in the Na coordination environment.

At 0.84 GPa just before superhydration, the sodium cation is coordinated by four framework oxygens and two water molecules with a strong Na—O2 bond with an interatomic distance of 2.31(2) Å (see Table 2). After superhydration at 1.51 GPa, the sodium coordination changes to sevenfold by binding an additional water molecule, which weakens the bonding between the sodium and the framework oxygens. The shortest bonding distance to the framework oxygen (Na—O2) is now 2.47(2) Å with the distance to the new water oxygen (Na—OW2) being 2.53(3) Å (Table 2). As a result, the sodium cations in the superhydrated natrolite have stronger interactions with water molecules than the framework oxygens; the sodium to framework oxygen distances range from 2.47(2) to 2.68(2) Å whereas the interatomic distances to water oxygens are within 2.40(4) and 2.53(3) Å (Table 2). This is analogous to the Ca-bonding in mesolite and scolecite where the Ca cations are strongly coordinated by three water molecules (2.31–2.36 Å) and to a lesser extent to four framework oxygens (2.50–2.54 Å). These results indicate that superhydration and the associated increase of the pore openings, as well as the decrease in the Na to framework oxygen interaction, will cause modifications to the ion exchange properties in this class of small-pore zeolites.

The structure of the water molecules inside the aluminosilicate channels after superhydration (FIG. 9) are also significant. Before superhydration (FIG. 8), there are no hydrogen bonds between water molecules whereas upon superhydration every water molecule is hydrogen bonded to exactly three nearest-neighboring waters. The first two hydrogen bonds form inside the channel with O—O interatomic distances of 2.80(4) and 3.09(4) Å and O—O—O angles of 104(2) and 112(1)° (according to the 1.51 GPa model, Table 2). This results in the formation of a helical water nanotube along the natrolite channel with sodium cations inside. The other hydrogen bond is relatively weak (3.14(3) Å, 1.51 GPa model) and interconnects neighboring water nanotubes across the channel wall via the $T_{10}O_{20}$ window.

TABLE 2

Selected interatomic distances (Å) and angles () for natrolite as a function of pressure.[a]

| | 0.40 GPa | 0.84 GPa | 1.51 GPa | 1.72 GPa | 2.42 GPa | 3.58 GPa | 5.01 GPa |
|---|---|---|---|---|---|---|---|
| Si(1)-O(1) | 1.6198(3) | 1.6199(2) | 1.6200(3) | 1.6200(1) | 1.6211(13) | 1.6199(5) | 1.6201(5) |
| Si(1)-O(5) | 1.6198(3) | 1.6199(2) | 1.6200(3) | 1.6200(1) | 1.6213(13) | 1.6199(5) | 1.6200(5) |
| mean | 1.6198(2) | 1.6199(1) | 1.6200(2) | 1.6200(2) | 1.6212(9) | 1.6199(4) | 1.6201(4) |
| Si(2)-O(2) | 1.6197(4) | 1.6197(3) | 1.6198(4) | 1.6197(2) | 1.6199(18) | 1.6196(7) | 1.6196(7) |
| Si(2)-O(3) | 1.6198(4) | 1.6198(3) | 1.6198(4) | 1.6198(2) | 1.6205(18) | 1.6197(7) | 1.6201(7) |
| Si(2)-O(4) | 1.6197(4) | 1.6198(3) | 1.6198(4) | 1.6198(2) | 1.6213(18) | 1.6197(7) | 1.6197(7) |
| Si(2)-O(5) | 1.6198(4) | 1.6198(4) | 1.6198(4) | 1.6198(2) | 1.6235(18) | 1.6199(7) | 1.6198(7) |
| mean | 1.6198(2) | 1.6198(2) | 1.6198(2) | 1.6198(1) | 1.6213(9) | 1.6197(4) | 1.6198(4) |
| Al-O(1) | 1.7498(4) | 1.7498(4) | 1.7498(4) | 1.7498(2) | 1.7521(18) | 1.7499(7) | 1.7500(7) |
| Al-O(2) | 1.7497(4) | 1.7497(3) | 1.7498(4) | 1.7497(2) | 1.7493(18) | 1.7493(7) | 1.7494(7) |
| Al-O(3) | 1.7498(4) | 1.7498(3) | 1.7498(4) | 1.7498(2) | 1.7519(18) | 1.7498(7) | 1.7500(7) |
| Al-O(4) | 1.7497(4) | 1.7498(3) | 1.7498(4) | 1.7498(2) | 1.7503(18) | 1.7497(7) | 1.7498(7) |
| mean | 1.7498(2) | 1.7498(2) | 1.7498(2) | 1.7498(1) | 1.7509(9) | 1.7497(4) | 1.7498(4) |
| Si(1)-O(1)-Al | 143.8(1) | 142.9(1) | 141.5(1) | 141.4(1) | 141.9(5) | 140.4(2) | 138.6(2) |
| Si(2)-O(2)-Al | 130.3(2) | 130.9(2) | 129.3(1) | 129.2(1) | 127.2(4) | 125.0(2) | 122.5(1) |
| Si(2)-O(3)-Al | 138.1(2) | 137.3(2) | 136.6(2) | 136.5(1) | 136.6(7) | 136.3(3) | 135.6(3) |
| Si(2)-O(4)-Al | 139.0(2) | 138.5(1) | 137.0(2) | 137.1(1) | 138.2(7) | 136.1(3) | 133.9(3) |
| Si(1)-O(5)-Si(2) | 146.3(1) | 145.2(1) | 143.6(1) | 143.61(8) | 143.7(5) | 142.5(2) | 140.3(2) |
| Na-O(2) | 2.40(1) | 2.31(1) | 2.47(2) | 2.57(2) | 2.77(2) | 2.36(2) | 2.31(1) |
| | 2.62(1) | 2.68(2) | 2.68(2) | 2.56(2) | 2.27(2) | 2.47(2) | 2.45(1) |
| Na-O(3) | 2.35(1) | 2.37(2) | 2.60(2) | 2.53(2) | 2.31(2) | 2.64(2) | 2.64(1) |
| Na-O(4) | 2.38(1) | 2.33(2) | 2.66(2) | 2.73(2) | 2.83(2) | 2.77(1) | 2.72(1) |
| OW1-O(1) | 2.88(2) | 2.88(3) | 2.87(5) | 2.81(4) | 2.80(4) | 2.83(3) | 2.88(3) |
| OW1-O(2) | 3.25(2) | 3.08(5) | 3.22(7) | 3.28(5) | 3.24(6) | 3.22(4) | 3.18(4) |
| OW1-O(5) | 2.98(2) | 2.98(4) | 3.11(5) | 3.15(4) | 2.95(5) | 2.98(4) | 2.97(3) |
| OW1-Na | 2.42(2) | 2.29(4) | 2.47(4) | 2.57(4) | 2.80(5) | 2.45(3) | 2.36(3) |
| | 2.42(3) | 2.55(4) | 2.40(4) | 2.31(4) | 2.33(4) | 2.37(3) | 2.37(3) |
| OW1-OW2 | | | 3.09(4) | 2.97(4) | 2.88(3) | 3.00(2) | 2.92(2) |
| | | | 2.80(4) | 2.91(4) | 3.05(4) | 2.89(3) | 2.94(2) |
| OW2-O(1) | | | 2.99(3) | 2.97(3) | 2.93(3) | 2.99(2) | 2.86(2) |
| OW2-O(2) | | | 3.02(3) | 3.00(3) | 2.65(3) | 2.96(2) | 2.91(2) |
| | | | 3.10(3) | 3.10(3) | 3.18(4) | 2.96(2) | 2.83(2) |
| OW2-O(3) | | | 2.83(4) | 2.90(3) | 3.15(4) | 2.74(2) | 2.85(2) |
| OW2-O(4) | | | 2.83(4) | 2.78(3) | 2.58(4) | 2.79(2) | 2.50(2) |
| OW2-O(5) | | | 3.08(3) | 2.97(3) | 3.09(4) | 2.96(2) | 3.05(2) |
| OW2-Na | | | 2.53(3) | 2.51(3) | 2.47(3) | 2.39(2) | 2.58(2) |

[a]Estimated standard deviations (ESD's) are in parentheses.

The helical water nanotube can be described as having a negatively charged exterior near the aluminosilicate framework and positively charged sodium cations inside. This suggests that these water molecules are highly oriented within and between the nanotubes. This helical water nanotube is responsible for the anomalous increase in the water diffusion at high pressure. It has also been found that changes in local channel polarity and solvent conditions can be used to modify the water occupancy and its conductivity inside a carbon nanotube.

It is believed that the water diffusivity of the superhydrated natrolite can be tuned by changes in the composition of the non-framework cations or the framework Al/Si ratio (and possibly framework composition). Furthermore, increase in the channel diameter or the compression of the increased number of water molecules may induce formation of different water structures as demonstrated in the example of ordered ice nanotubes inside various sizes of carbon nanotubes. The conditions used for superhydration in this work resemble part of the cold oceanic lithosphere during subduction, which implies zeolite superhydration should be considered as a possible mechanism for the storage and transport of water into the Earth's upper mantle.

The water contents of K—GaSi-NAT and Na—AlSi-NAT double under pressure leading to superhydration; for K—GaSi-NAT the refined unit cell composition before and after the pressure experiment are $K_{7.5(3)}Ga_{8.0(1)}Si_{12.0(1)}O_{40} \cdot 6.3(6)H_2O$ and $K_{7.9(5)}Ga_8Si_{12}O_{40} \cdot 12.2(16)H_2O$, respectively (see Table 3). Upon superhydration, a new water site OW3, which is in close proximity to statistically distributed potassium cation sites, is partially occupied. Subsequently, the potassium ions in the middle of the $T_{10}O_{20}$ window (K1 site) migrate to the remaining potassium sites (K1A, K1B and K1C). The occupancies of the initial water sites, OW1 and OW2, increase by 64% and 35%, respectively, and all of the water molecules including those located at the OW3 site coordinate the potassium cations with interatomic distances in the range between 2.45(12) and 3.35(13) Å (see Table 4).

As a consequence, the average potassium-to-framework oxygen distance range increases from 2.661(4)–2.794(9) Å before superhydration to 2.71(1)–2.92(2) Å. The overall rotation angle of the fibrous chains ($\psi$, see FIG. 1) decreases from 17.5(1)° to 17.0(1)° after superhydration. This is similar to, although smaller than, the pressure-induced evolution of the $\psi$ parameter observed in Na—AlSi-NAT and indicates that superhydration is coupled to the relaxation of the overall framework distortion by expanding the pore space along the channel; in fact, the opening of the channel, defined by the shortest and longest interatomic distances between two chain-bridging oxygens (O(1), see FIG. 1), increases from 5.70(1)×9.54(1) Å to 5.80(1)×9.57(1) Å before and after superhydration, respectively. The degree of the overall chain rotation is, however, much less than those observed in the aluminosilicate natrolite (23.7(1)°~26.4(1)°). The reason for this is attributed to the combined effect of the different non-framework cation distribution and the increased flexibility of the T-O-T angles in K—GaSi-NAT compared to Na—AlSi-NAT. The latter may also explain the 3-dimensional swelling unique to the gallosilicate natrolite. Given the higher flexibility of the T-O-T angle in a gallosilicate framework, incorporation of additional water molecules into the channels at high pressure would induce the T-O-T angles within the fibrous chain (T-O(2)-T and T-O(3)-T) to relax together with the angles between the chains (T-O(1)-T, see Table 4).

TABLE 3

Atomic coordinates and estimated standard deviations of K-GaSi-NAT at ambient conditions[a]) and after superhydration[b] (non-shaded, recovered from 1.9 GPa).

| atom | site | p | x[c] | y[c] | z[c] | $U_{(eq)}$[d] |
|---|---|---|---|---|---|---|
| T(1) | 4a | 1.000[e] | 0 | 0 | 0 | 8 (1) |
|  |  | 1.000[f] | 0 | 0 | 0 | 30 (3) |
| T(2) | 16e | 1.000[e] | −319 (1) | 1324 (1) | 6176 (2) | 11 (1) |
|  |  | 1.000[f] | −317 (3) | 1330 (3) | 6182 (7) | 31 (2) |
| O(1) | 8d | 1.000 | 5787 (5) | 2500 | 1250 | 32 (2) |
|  |  | 1.000 | 5766 (14) | 2500 | 1250 | 53 (7) |
| O(2) | 16e | 1.000 | 574 (4) | 1280 (4) | 4375 (8) | 26 (2) |
|  |  | 1.000 | 586 (15) | 1280 (12) | 4422 (26) | 59 (7) |
| O(3) | 16e | 1.000 | 121 (4) | 1054 (4) | 8559 (8) | 26 (2) |
|  |  | 1.000 | 126 (13) | 1053 (13) | 8549 (26) | 57 (6) |
| K(1)[g] | 8d | 0.250(11) | −611 (11) | 2500 | 1250 | 22 (2) |
| K(1A)[g] | 8d | 0.338(4) | −182 (10) | 2500 | 1250 | 22 (2) |
|  |  | 0.363(12) | −466 (30) | 2500 | 1250 | 45 (7) |
| K(1B)[g] | 8d | 0.266(11) | 432 (10) | 2500 | 1250 | 22 (2) |
|  |  | 0.412(30) | 189 (24) | 2500 | 1250 | 45 (7) |
| K(1C)[g] | 8d | 0.081(7) | 980 (30) | 2500 | 1250 | 22 (2) |
|  |  | 0.214(20) | 813 (43) | 2500 | 1250 | 45 (7) |
| OW(1)[h] | 8d | 0.28(4) | 2060 (60) | 2500 | 1250 | 120 (20) |
|  |  | 0.46(5) | 1969 (86) | 2500 | 1250 | 146 (28) |
| OW(2)[h] | 8d | 0.51(4) | 2780 (30) | 2500 | 1250 | 117 (15) |
|  |  | 0.69(8) | 2813 (58) | 2500 | 1250 | 146 (28) |
| OW(3)[h] | 8d | 0.38(7) | −1174 (121) | 2500 | 1250 | 146 (28) |

[a]$I\bar{4}$ 2d, a = 13.639(2) Å, c = 6.545(1) Å.
[b]$I\bar{4}$ 2d, a = 13.751(2) Å, c = 6.605(1) Å.
[c]×10$^4$.
[d]Å$^2$ × 10$^3$, $U_{(eq)}$ is defined as one third of the trace of the orthogonalized $U_{ij}$ tensor.
[e]Gallium occupancy refined to 0.399(7).
[f]Gallium occupancy fixed to 0.399.
[g,h]Isotropic displacement factors constrained to be equal.

TABLE 4

Selected interatomic distances (Å) and angles ( ) of K-GaSi-NAT at ambient conditions and after superhydration (non-shaded, recovered from 1.9 GPa).[a]

| | | | |
|---|---|---|---|
| T(1) - O(3) | 1.745(18) × 4 | Av. O - T(1) - O | 109.5(1)[b] |
| T(2) - O(2) | 1.702(18) | Av. O - T(2) - O | 109.5(1)[b] |
| T(2) - O(2) | 1.720(18) | T(2) - O(1) - T(2) | 138.0(12) |
| T(2) - O(3) | 1.720(19) | T(2) - O(2) - T(2) | 128.6(9) |
| T(2) - O(1) | 1.724(8) | T(1) - O(3) - T(2) | 130.4(11) |
| Av. T(2) - O | 1.717(8)[b] | | |
| K(1) - O(3) | | K(1) - OW(1) | |
| | | K(1) - OW(2) | |
| K(1) - O(2) | | K(1A) - OW(1) | |
| | | K(1B) - OW(2) | |
| K(1A) - O(2) | 3.049(27) × 2 | K(1C) - OW(2) | |
| | | OW(1) - OW(2)* | |
| K(1A) - O(3) | 2.793(21) × 2 | K(1A) - OW(1) | 3.33(5) × 2 |
| K(1B) - O(2) | 2.739(18) × 2 | K(1A) - OW(2) | 3.35(13) |
| K(1B) - O(3) | 2.674(17) × 2 | K(1B) - OW(1) | 3.28(4) × 2 |
| K(1C) - O(2) | 2.702(18) × 2 | K(1C) - OW(2) | 2.45(12) |
| | | K(1C) - OW(3) | 2.75(9) |
| K(1C) - O(3) | 2.835(27) × 2 | OW(1) - OW(3) | 2.73(18) |
| | | OW(2) - OW(3) | 2.57(21) |
| | | OW(1) - OW(2)* | 2.50(19) |
| | | | 1.16(9) |

[a]Estimated standard deviations are in parentheses

[b]Standard deviations computed using $\sigma = \frac{1}{n}\left[\sum_{i=1}^{n}\sigma_i\right]^{\frac{1}{2}}$

Pressure-induced Cation Disordering

Temperature-induced cation disordering occurs in mesolite as a result of changes in Ca coordination. Upon heating, one of the Ca-coordinating waters, unique in the Ca layer, starts to be expelled preferentially. Complete exclusion of the water results in the reduction of the Ca-coordination number from seven to six, which is the same as the Na-coordination number in the Na layer. As a consequence, Ca and Na atoms can then randomly occupy the former Na sites in the natrolite cell, with the water molecules fully occupying the natrolite water site. At this stage, there is no distinction between the natrolite and scolecite layers along the b-axis, and this is indicated by the disappearance of the mesolite superlattice reflections.

Assuming that the volume expansion in mesolite indicates superhydration, the mechanism of the pressure-induced cation disordering must be different from its temperature-driven analogue. Superhydration in mesolite is likely to occur preferentially in the Na layer rather than in the Ca layer since the latter already contains 50% more water at ambient conditions. This causes an increase in the Na-coordination number from six to seven, as in natrolite, which makes the Na coordination shell compatible to the Ca shell. This facilitates cross-channel diffusion and subsequent disordering of both cations. The slight increase in the volume before the disappearance of the superlattice reflections implies that the cation disordering is a continuous transition driven by diffusion processes, and the reappearance of the superlattice reflections upon pressure release indicates reversible hydration/dehydration.

Hydrostatic Pressure-induced Partial Amorphization

Using KBr as a solid pressure transmission media, pressure-induced amorphizations in scolecite and mesolite have been reported. In the absence of the pore-penetrating molecules such as water, both samples showed progressive reduction in intensity and broadening of the X-ray and Raman peaks without any indications of phase transitions and completely amorphized above 10 GPa. These transitions were described as irreversible and the pressure-quenched products were similar to the temperature-quenched aluminosilicate glasses. The results of the five separate high-pressure runs of scolecite in Example 3 (see FIG. 14) are also indicative, although not conclusive, of the effects of a hydrostatic pressure-induced amorphization. There is a 40% reduction of $I_{(021)}$ and a 30% increase in the $FWHM_{(021)}$ between 0.52 and 2.60 GPa, while the width of the R1 ruby emission line did not show any broadening. Important differences between these results and those obtained using KBr can be attributed to the choice of the pressure medium. The solid pressure medium produces quasi-hydrostatic pressures and shear stress on the sample whereas the alcohol and water mixture in the optimum ratio provide much better hydrostatic conditions. Furthermore, the ability of the water molecules to penetrate the nanopore space and interact with the species inside provides an additional variable in the high-pressure phase transitions.

Unlike the results obtained using KBr, tests conducted using aqueous mixtures showed volume expansion in scolecite above 2 GPa (3% increase on $d_{(021)}$ between 0.52 and 2.60 GPa data), which is in line with the superhydration or volume expansion behaviors found in natrolite and mesolite. Furthermore, the reappearance of the peaks at similar d-spacings upon decompression indicates that the local structures are maintained throughout the X-ray amorphous region, which may suggest that shear stress is not the major cause for the amorphization. A similar phenomenon has been shown to occur in zeolite LTA (Linde Type A), and these materials are said to have a structural memory or templating non-deformable units about which the original crystal structure can be restructured upon pressure release.

Three-dimensional Swelling and Irreversible Volume-Expansion

The different type of pressure-induced expansion observed in the potassium gallosilicate natrolite is believed to be attributed to the different cation and water distribution in the starting materials. Unlike natrolite, mesolite and scolecite, the potassium cations in the gallosilicate natrolite occupy the sites close to the channel walls bound by the $T_{10}O_{20}$ windows, and the sites along the channels host disordered water molecules at ambient conditions. The cation distribution in the gallosilicate natrolite likely remains more or less the same throughout the volume expansion at high pressures since there are no major changes in the relative peak intensities. If additional water molecules are added at high pressure to drive the observed three-dimensional volume-expansion, the resulting pore water must have a different structure to the one observed in superhydrated natrolite. In addition to the different distribution of the non-framework species, another reason for the three-dimensional swelling in the gallosilicate natrolite can be attributed to the flexibility of the T-O-T angles in a Ga/Si framework compared to its Al/Si counterpart.

Due to the substitution of the larger Ga for Al, the T-O-T angles in the gallosilicate frameworks show greater degrees of distortions than those of the aluminosilicates. Given the higher flexibility of the T-O-T angle in a gallosilicate framework, incorporation of additional water molecules into the channels at high pressure would exert the T-O-T angles within the fibrous chain to relax along with the angles between the chains. Due to these characteristics, the expanded gallosilicate phase at high pressures is found to be metastable under ambient conditions. The preservation of the expanded phase after decompression, which is presumably superhydrated, implies the potential use of similar systems with a superhydration at lower pressures as, for example, a storage media for the tritiated water (THO) from nuclear processing facilities.

Captured Transition and Rare Earth Metal Ions as Contrast Agents for the Gastrointestinal Tract Paramagnetic ions captured in microporous materials are particularly useful for imaging studies in human beings. The invention overcomes the problems associated with toxicity of some of the paramagnetic metals considered most useful for MRI studies, for example trivalent gadolinium. Toxicity of trivalent gadolinium has been reduced by combining it with dimethyltetraminopenta-acidic acid to form complex that exhibits less toxicity than the gadolinium salt. Examples of other ions that can be used include divalent manganese, tetravalent vanadium, trivalent vanadium, divalent copper, divalent nickel, trivalent chromium, divalent cobalt, divalent iron, trivalent iron and trivalent cobalt. These examples are not intended to be limiting and other species capable of ion exchanging include members of the lanthamide series of elements and the rare earth elements.

The amount of metal ion enclosed within the microporous material will depend on the swelling characteristics of the particular material used, as well as the amount of pressure that is applied. The preferential capture of paramagnetic ions such as $Gd^{+3}$ and $Mn^{+2}$ is sufficient to give excellent MRI imaging properties when the ion captured in the microporous material is used for imaging studies.

Paramagnetic ions captured in microporous materials are particularly useful for MRI studies of the gastrointestinal tract, especially since pharmaceutically acceptable preparations of these materials can be administered enterically, for example, by nasogastric tube to either an animal or a human being. Oral administration is preferred for most applications involving studies or treatment of humans.

Detection of the paramagnetic ion captured in a microporous material after administration is most preferably performed by magnetic resonance imaging, although conventional radiographic imaging and computed tomography (CT) imaging may also be employed similar to methods used with $BaSO_4$ and gastrographin imaging. High Z (atomic weight) metals like gadolinium may also be detected by monochromatic x-ray sources, for example, K-edge imaging.

In a most preferred method of practice, the invention is used for gastrointestinal tract imaging. A pharmaceutically acceptable formulation including trivalent gadolinium captured in a microporous material is administered, preferably orally, to a human or animal and detected by magnetic resonance imaging. The microporous material is prepared in a pharmaceutical carrier.

The paramagnetic ions captured in the microporous materials of this invention may be combined with pharmaceutically acceptable formulating agents, dispersing agents and fillers. Powders, granules, capsules, coated tablets, syrupy preparations and aqueous suspensions may be utilized for oral preparations. Formulating agents employed may be either solid or liquid, including but not limited to such solids as calcium phosphate, calcium carbonate, dextrose, sucrose, dextrin, sucrose ester, starch, sorbitol, mannitol, crystalline cellulose, talc, kaolin, synthetic aluminum silicate, carboxymethyl cellulose, methylcellulose, cellulose acetate phthalate, alginates, polyvinyl pyrrolidone, polyvinyl alcohol, gum arabic, tragacanth gum, gelatin, bentonite, agar powder, shellac, Tween 80, carrageenans and psyllium.

Administration is most preferably oral because of better patient acceptance in that form but administration may also be enteric, vaginal, anal or by direct introduction into the gastrointestinal tract at any point such as by introduction through tubes accessing the alimentary canal. Examples of nonoral use include retrograde pelvic studies and investigations to define vaginal contents. Flavor enhancers may be added to oral preparations, including taste masking substances such as sweeteners and citrus flavors. Other additives, including color, preservatives, bulk or antifoam agents may also be included in the formulation.

The invention may also be used in conjunction with magnetic resonance imaging of body surfaces. For example, artificial limbs must be custom fitted to leg, arm, hand or foot amputees. Present methods are time-consuming and rendered difficult because photographs show only skin surface while x-ray indicates only dense material such as bone. MRI could show both bone and skin and therefore facilitate design of a prosthetic device which must be customized to the remaining member of the body. Zeolite enclosed trivalent gadolinium would be ideal for this purpose. The crystalline material would be powdered sufficiently to be conveniently applied to a skin surface, preferably as an aerosol which could be either a dry powder or a suspension in a suitable fluid, for example water or alcohol. The skin is preferably first treated with an agent that promotes adherence of the powder to the surface, for example, tincture of benzoin. Other applications envisioned are imaging of the foot, useful in customizing footwear for abnormal or injured feet. Surface imaging could also be used in connection with inanimate surfaces, for example some metal surfaces. In some cases, especially where high resolution was desired, uniform application would be important so that surface roughness reflected the surface examined rather than an artifact of uneven application.

The invention may also be used to evaluate lung ventilation. An aerosol of suitably small particles, in the nanometer range, would be inhaled by the patient prior to MRI scans to determine lung ventilation.

The paramagnetic ion captured in a microporous material of this invention will typically be formulated as suspensions or dispersions, preferably in EZ dispersant (available from E-ZM Company) or used as the supernatant from pharmacy-purchased suspensions of $BaSO_4$ under the trade name of EZpaque) at a low weight to volume ratio. For oral administration this is preferably approximately one percent Higher concentrations of the zeolite composition may be prepared as suspensions; however, for MR imaging purposes, image intensity decreases markedly above weight ratios of 1%. The 1% suspensions in EZpaque supernatant appear to be stable indefinitely.

A marked advantage of calcium gadolinium captured in a microporous material is the relatively low concentration that may be employed in a dispersing medium. For example, a one percent concentration of calcium gadolinium captured in a microporous material administered orally is effective in producing excellent images for MRI studies, although higher weight percent concentrations may be utilized in accordance with the form of the preparation. In contrast, when barium sulfate is used in the same dispersing medium, concentrations of up to 40–50% by weight are required and precipitation is often a problem.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

The invention claimed is:

1. A method of capturing specified materials, wherein the specified materials are atoms, molecules, ions or a combination thereof, the method comprising:
   a) contacting a microporous material, capable of undergoing a temporary structural distortion which alters resting lattice dimensions under increased ambient pressure and at least partially returning to rest lattice dimensions when returned to ambient pressure, with a hydrostatic fluid having at least one specified material carried therein, under pressure which structurally distorts said lattice sufficiently to permit entry of said at least one specified material, wherein the microporous material is a Zn-containing form of Linde A zeolite having the molecular structure $Zn_6[Al_{12}Si_{12}O_{48}]$ $29H_2O$; and
   b) reducing pressure of said fluid to permit return to at least partial resting lattice dimension while said at least one specified material is therein;
whereby said at least one specified material is captured in said microporous material to form a modified microporous material.

2. The method of incorporating specified materials in microporous materials according to claim 1, wherein the increased ambient pressure is maintained for at least 30 minutes.

3. The method of incorporating specified materials in microporous materials according to claim 1, wherein the hydrostatic fluid comprises water, water and methanol, water and ethanol or a combination of water, methanol and ethanol.

4. The method of incorporating specified materials in microporous materials according to claim 1, wherein the hydrostatic fluid comprises from about 50 to about 95 weight percent methanol, from about 5 to about 40 weight percent ethanol and from about 1 to about 25 weight percent water.

5. The method of incorporating specified materials in microporous materials according to claim 1, wherein the hydrostatic fluid comprises from about 75 to about 85 weight percent methanol, from about 10 to about 25 weight percent ethanol and from about 2 to about 8 weight percent water.

6. The method of incorporating specified materials in microporous materials according to claim 1, wherein the modified microporous material has an increased number of water molecules.

7. The method of incorporating specified materials in microporous materials according to claim 1, wherein the pressure is increased up to about 0.6 gigapascals (GPa).

8. A method of capturing specified materials, wherein the specified materials are atoms, molecules, ions or a combination thereof, the method comprising:
   a) contacting a microporous material, capable of undergoing a temporary structural distortion which alters resting lattice dimensions under increased ambient pressure and at least partially returning to rest lattice dimensions when returned to ambient pressure, with a hydrostatic fluid having at least one specified material carried therein, under pressure which structurally distorts said lattice sufficiently to permit entry of said at least one specified material, wherein the microporous material is a lithium exchanged Linde A zeolite, having the molecular structure $Li_{12}[Al_{12}Si_{12}O_{48}]$ $29H_2O$; and
   b) reducing pressure of said fluid to permit return to at least partial resting lattice dimension while said at least one specified material is therein;
whereby said at least one specified material is captured in said microporous material to form a modified microporous material.

9. The method of incorporating specified materials in microporous materials according to claim 8, wherein the pressure is increased up to between about 1.5 to about 2.0 GPa.

10. The method of incorporating specified materials in microporous materials according to claim 1, wherein the specified materials are $Pb^{2+}$, $Gd^{3+}$, $Hg^{2+}$, $Cd^{2+}$, $Sr^{2+}$, $Cs^{+}$, $Ag^{+}$, $Ba^{2+}$, $Er^{3+}$, $Eu^{3+}$, $K^{+}$, $La^{3+}$, $NH_4^{+}$, $Na^{+}$, $Pd^{2+}$, $Rb^{2+}$, $Sn^{2+}$, $Te^{4+}$, $Tl^{+}$, $Tm^{3+}$, $Y^{3+}$, $Yb^{3+}$ or $Zn^{2+}$.

11. The method of incorporating specified materials in microporous materials according to claim 1, wherein the modified microporous material has a unit cell volume greater than the unit cell volume of the microporous material.

12. The method of incorporating specified materials in microporous materials according to claim 1, wherein the specified materials remain incorporated in the modified microporous material at pressures below 0.1 GPa.

13. The method of incorporating specified materials in microporous materials according to claim 8, wherein the increased ambient pressure is maintained for at least 30 minutes.

14. The method of incorporating specified materials in microporous materials according to claim 8, wherein the hydrostatic fluid comprises water, water and methanol, water and ethanol or a combination of water, methanol and ethanol.

15. The method of incorporating specified materials in microporous materials according to claim 8, wherein the hydrostatic fluid comprises from about 50 to about 95 weight percent methanol, from about 5 to about 40 weight percent ethanol and from about 1 to about 25 weight percent water.

16. The method of incorporating specified materials in microporous materials according to claim 8, wherein the hydrostatic fluid comprises from about 75 to about 85 weight percent methanol, from about 10 to about 25 weight percent ethanol and from about 2 to about 8 weight percent water.

17. The method of incorporating specified materials in microporous materials according to claim 8, wherein the modified microporous material has an increased number of water molecules.

18. The method of incorporating specified materials in microporous materials according to claim 8, wherein the specified materials are $Pb^{2+}$, $Gd^{3+}$, $Hg^{2+}$, $Cd^{2+}$, $Sr^{2+}$, $Cs^{+}$, $Ag^+$, $Ba^{2+}$, $Er^{3+}$, $Eu^{3+}$, $K^+$, $La^{3+}$, $NH^{4+}$, $Na^+$, $Pd^{2+}$, $R^{2+}$, $Sn^{2+}$, $Te^{4+}$, $Tl^+$, $Tm^{3+}$, $Y^{3+}$, $Yb^{3+}$, or $Zn^{2+}$.

19. The method of incorporating specified materials in microporous materials according to claim 8, wherein the modified microporous material has a unit cell volume greater than the unit cell volume of the microporous material.

20. The method of incorporating specified materials in microporous materials according to claim 8, wherein the specified materials remain incorporated in the modified microporous material at pressures below 0.1 GPa.

* * * * *